United States Patent [19]
Bonyhadi et al.

[11] Patent Number: 5,601,975
[45] Date of Patent: Feb. 11, 1997

[54] METHOD FOR SCREENING POTENTIAL THERAPEUTICALLY EFFECTIVE ANTIVIRAL AGENTS

[75] Inventors: Mark L. Bonyhadi, Belmont; Joseph M. McCune, San Francisco; Hideto Kaneshima, Palo Alto, all of Calif.

[73] Assignee: SyStemix, Inc., Palo Alto, Calif.

[21] Appl. No.: 466,420

[22] Filed: Jun. 6, 1995

Related U.S. Application Data

[62] Division of Ser. No. 109,305, Aug. 19, 1993.

[51] Int. Cl.$^6$ .................................................. C12Q 1/70
[52] U.S. Cl. .................................................. 435/5; 435/974
[58] Field of Search .......................... 435/240.1–240.241, 435/974, 5

[56] References Cited

FOREIGN PATENT DOCUMENTS

WO91/16910  11/1991  WIPO .

OTHER PUBLICATIONS

Riesenfeld et al. "Spontaneous and Induced Appearance of Murine Leukemia Virus Antigen Containing Cells in Organ Cultures of Embryonic Mouse Thymus" *International Journal of Cancer*, vol. 20, No. 2(15 Aug. 1977) pp. 309–317.
Hays et al. "Mechanisms of Thymic Lymphomagenesis by the Retrovirus SL3–3" *Cancer Research*, vol. 50, No. 17 Suppl(1 Sep. 1990) pp. 5631S–5635S.
Tanaka et al. "HIV–1 Infection of Human Fetal Thymocytes" *Journal of Acquired Immune Deficiency Syndromes*, vol. 5, No. 1(1992), pp. 94–101.
Jenkinson et al. "T–Cell Differentiation in Thymus Organ Cultures" *Seminars in Immunology*, vol. 2(1990), pp. 51–58.
Rosenzweig et al. "Thymocytes and Macrophages are Targets of HIV–1 Infection in the Neonatal Thymus" *National Conference on Human Retroviruses and Related Infections* (Meeting Abstract) (1st), (1993). p. 103.
Barry et al., "Successful engraftment of human postnatal thymus in severe combined immune deficient (SCID) mice: Differential engraftment of thymic components with irradiation versus anti–asialo GM–1 immunosuppressive regiments" *J. Exp. Med.* (1991) 173:167–180.
Bauer et al., "Mini organ culture of thyroid tissue: A new technique for maintaining the structural and functional integrity of thyroid tissue in vitro" *Lab. Invest.* (1988) 59:281–291.
Davidson et al., "Kinetics of chicken embryonic thymocyte development in ovo and in organ culture" *Eur. J. Immunol.* (1992) 22:1429–1435.
Davidson et al., "Chicken Fetal Thymus Organ Culture. A model for T–cell development within the thymic microenvironment" *Lymphatic Tissues and in Vivo Immune Responses*, Ezine, S., et al., eds., Marcel Dekker, Inc., New York (1991) pp. 89–94.
Davidson et al., "Delineation of chicken thymocytes by CD3–TCR complex, CD4 and CD8 antigen expression reveals phylogenetically conserved and novel thymocyte subsets" *Int. Immunol.* (1992) 4:1175–1182.

Fisher et al., "Human thymocyte development in mouse organ cultures" *Int. Immunol.* (1990) 2:571–578.
Hendrickson et al., "A link between double–strand break–related repair and V(D)J recombination: The scid mutation" *Proc. Natl. Acad. USA* (1991) 88:4061–4065.
Jenkinson et al., "T–cell differentiation in thymus organ cultures" *Immunol.* (1990) 2:51–58.
Kyoizumi et al., "Implantation and maintenance of functional human bone marrow in SCID–hu mice" *Blood* (1992) 79:1704–1711.
Merkenschlager et al., "Selective manipulation of the human T–cell receptor repertoire expressed by thymocytes in organ culture" *Proc. Natl. Acad. Sci. USA* (1992) 89:4255–4259.
Merkenschlager et al., "Human postnatal thymocytes generate phenotypically immature $CD3^{dim}$, $CD5^{dim}$, $CD1a^{bright}$ progeny in organ culture" *J. Immunol.* (1992) 148:1012–1015.
Namikawa et al., "Long–term human hematopoiesis in the SCID–hu mouse" *J. Exp. Med.* (1990) 172:1055–1063.
Péault et al., "Lymphoid reconstitution of the human fetal thymus in SCID mice with $CD34^+$precursor cells" *J. Exp. Med.* (1991) 174:1283–1286.
Schiff et al., "Organ culture of adult rat colonic mucosa on fibrin foam" *In Vitro* (1980) 16:893–906.
Smith et al., "Antibodies to CD3/T–cell receptor complex induce death by apoptosis in immature T cells in thymic cultures" *Nature* (1989) 337:181–184.
Spangrude et al., "Differentiation of hematopoietic stem cells in irradiated mouse thymic lobes" *J. Immunol.* (1990) 145:3661–3668.
Tanaka et al., "HIV–1 infection of human fetal thymocytes" *J. Aids* (1992) 5:94–101.
Terstappen et al., "Flow cytometric assessment of human T–cell differentiation in thymus and bone marrow" *Blood* (1992) 79:666–677.
Tuch et al., "Long–term organ culture of large numbers of human fetal pancreata: Analysis of their insulin secretion" *Diabet. Med.* (1987) 4:116–121.
Wilson et al., "Phenotypic analysis of the chicken thymic microenvironment during ontogenic development" *Dev. Immunol.* (1992) 2:19–27.
Mocarski et al., "Human cytomegalovirus in a SCID–hu mouse: Thymic epithelial cells are prominent targets of viral replication" *Proc. Natl. Acad. Sci. USA* (1993) 90:104–108.
Aldrovandi et al., "The SCID–hu mouse as a model for HIV–1 infection" *Nature* (1993) 363:732–736.
Gao et al., "Differential phosphorylation of Azidothymidine, Dideoxycytidine, and Dideoxyinosine in resting and activated peripheral blood mononuclear cells" *J. Clin. Invest.* (1993) 91:2326–2333.

*Primary Examiner*—Christine M. Nucker
*Assistant Examiner*—Jeffrey Stucker
*Attorney, Agent, or Firm*—Morrison & Foerster LLP

[57] ABSTRACT

The invention provides methods for screening agents for potential anti-viral effects by assessing the ability of the agents to suppress viral replication and/or pathology in thymic cells grown in thymic organ culture in vitro. Also provided are methods to study viral pathology and infectivity.

10 Claims, 13 Drawing Sheets

METHOD FOR SCREENING POTENTIAL THERAPEUTICALLY EFFECTIVE ANTIVIRAL AGENTS

This application is a division of application Ser. No. 08/109,305 filed Aug. 19, 1993.

DESCRIPTION

1. Technical Field

The present invention is directed to methods to screen potential therapeutic anti-viral agents, particularly those that suppress viral replication and/or pathology in thymus cells.

2. Background Art

The ability to obtain therapeutically effective anti-viral agents is facilitated by preclinical screening systems that are relevant, predictive and amenable to high throughput. Such systems include in vitro cell-free assays, in vitro tissue culture assays and assays in animal models. Important animal models have traditionally included laboratory mice, rats and non-human primates. More recently, specifically modified mice such as SCID-hu mice and hu-PBL mice have also played a role. However, even these higher-order models do not usually reflect human physiology in its entirety. Another drawback of animal testing is the need for extensive and direct contact with infected animals and, therefore, the potential exposure to drugs and viruses. This situation is particularly undesirable in the case of human immunodeficiency virus (HIV). Furthermore, animal systems are usually time consuming and expensive, making them unsuitable for rapid screening of large numbers of potential therapeutic agents.

For numerous viruses, there are no animal models; thus efficacy testing of putative therapeutic agents on human beings occurs only at the clinical stage. The extreme expense and safety concerns of this clinical testing pose a barrier to the current development of therapeutics and ultimate progress in delineating the mechanisms of viral infectivity and pathogenesis.

Although in vitro drug screening systems exist, drug efficacy results from in vitro cell-free and cell culture systems do not always correlate well with in vivo efficacy. Nevertheless, in vitro systems are essential in modern pharmaceutics for large-scale screening of agents with therapeutic potential. The more closely an in vitro system mimics in vivo infection, the more useful the in vitro assay. Thus, in vitro drug screening assays are constantly being developed to more closely mimic in vivo responses.

HIV is the name given to a group of highly related viruses which has been identified as the primary etiological agent of the acquired immunodeficiency syndrome (AIDS) and AIDS-related complex (ARC) in humans. HIV is a deadly infectious disease and a major worldwide health problem. Progress towards understanding the pathogenesis of HIV infection in vivo and discovering therapeutic agents has been hampered by a lack of a cost-effective, efficient, and clinically relevant in vitro screening system. One of the most widely-used animal models for HIV infection is the rhesus macaque and infection with simian immunodeficiency virus (SIV). In this system, large amounts of drugs must be synthesized and isolated prior to screening, an expensive and time consuming task. Maintaining the animals is expensive. Because of the high cost of the monkey model, it is only used to test drugs already showing strong indications of success in in vitro testing. Moreover, the monkey model utilizes a different, although related, virus, and it is not necessarily true that antiviral compounds active against SIV will be active against HIV, and vice versa.

What is needed to develop anti-viral agents is an effective in vitro screening system that reflects in vivo pathogenesis and which is capable of rapidly screening a wide variety of agents. Such an in vitro system should provide the reliability of the more expensive in vivo systems and yet afford rapid, cost-effective initial screening for potential therapeutics from a virtually limitless variety of sources. To the extent that such a system is relevant to HIV infection in vivo, it should also be useful for the evaluation of pathogenic mechanisms associated with HIV infection.

DISCLOSURE OF INVENTION

The present invention is directed to a method of screening agents for therapeutic potential. The method comprises incubating thymic lobules, preferably human fetal thymic lobules, for a time and under conditions sufficient to allow viral infection. The lobules are then exposed to a virus, and, either prior to virus exposure, simultaneously, or shortly thereafter, exposed to an agent to be screened. The lobule contents are then assayed for suppression of viral infection. Therapeutic potential is present if any indicia of viral infection are diminished relative to a control sample that has not been exposed to the agent.

The method can also be used to study viral transmission, infection, replication, and pathogenesis.

DEFINITIONS

The following definitions refer to terms and phrases used herein. Other definitions appear as indicated.

Suppression indicates that there is evidence of reduced viral transmission, infection, replication, or pathology.

Assaying cells for viral activity is done by observing any factors such as cell viability and yields and CD4 and CD8 phenotypes.

A control sample is one in which thymic lobules are obtained and incubated under identical conditions as the lobules to be infected but not exposed to the virus to be tested.

Pathology is viral infection, replication, cell death, slowing or aberrant cell growth or atypical cellular phenotype or function due to viral infection.

An anti-viral agent is one that prevents or treats viral infection, i.e., one that can be used prophylactically or therapeutically. Such an anti-viral agent can affect any of the mechanisms of virus transmission, infection, replication, or pathology.

A potential anti-viral agent is an agent which has been shown to suppress viral infection and/or pathology in the method described herein. Such a potential anti-viral agent has an enhanced likelihood of being effective in human prophylaxis and therapy. Potential anti-viral agents can come from a virtually limitless variety of sources.

Viral activity refers to viral infection, re-infection, replication, expression of viral proteins or pathology.

BRIEF DESCRIPTION OF DRAWINGS

FIG. 1 is discussed in Example 1.

FIG. 3 is discussed in Example 3.

FIG. 4 is discussed in Example 3.

FIG. 6 is discussed in Example 3.

FIG. 7 is discussed in Example 3.

FIG. 8 is discussed in Example 4.

FIG. 11 is discussed in Example 4.

FIG. 12 is discussed in Example 6.

FIG. 14 is discussed in Example 6.

FIG. 15 is discussed in Example 6.

FIG. 16 is discussed in Example 6.

MODES FOR CARRYING OUT THE INVENTION

Figure 1:
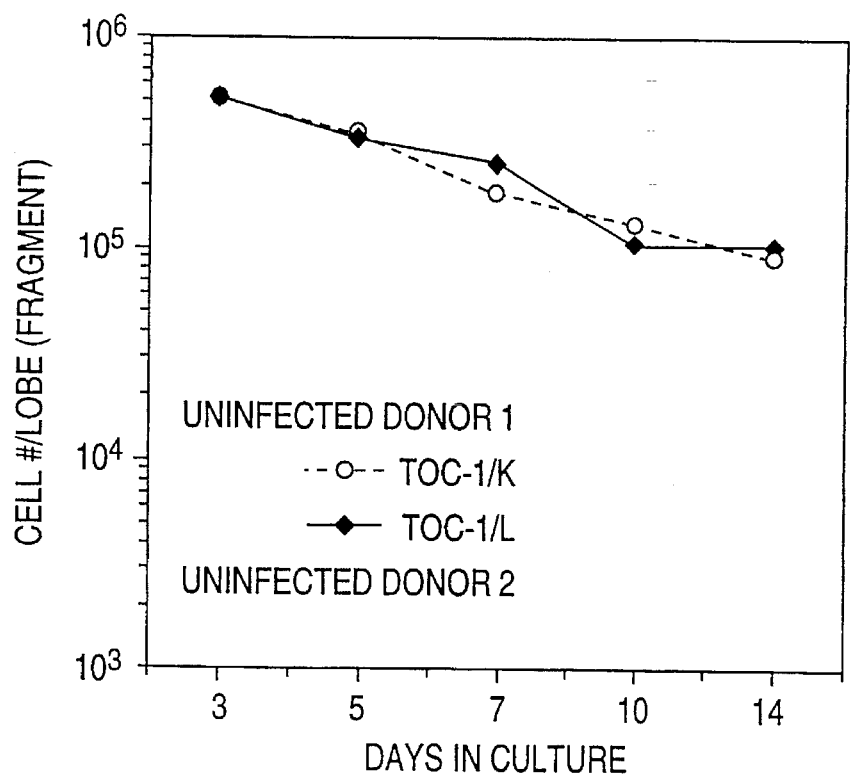
FIG. 1 is a graph depicting viable cell yields per incubated thymus fragment in uninfected cultures.

The present invention is directed to methods of screening agents for potential anti-viral efficacy and elucidating the mechanisms of viral infection, transmission, and pathogenesis.

It has now been found that HIV infection of cultures of intact human thymic lobules mimics the behavior of existing animal models for HIV infection, including the SCID-hu mouse. The system is also known as TOC for thymic organ culture. The TOC system is useful for rapid screening of compounds for anti-viral potential, particularly those for the treatment and prevention of AIDS. The TOC system is much simpler, safer, faster, and more cost effective than existing animal models. The TOC system is also more predictive of the actual efficacy of known anti-HIV compounds in humans than other in vitro systems.

Utilizing the TOC method described herein, known therapeutic agents have been found to exert therapeutic efficacy similar to that found in vivo. More specifically, both 2', 3'-dideoxyinosine (ddI) and azidothymidine (AZT; also referred to as zidovudine) suppressed HIV replication and pathology at equivalent dose ranges found to be active in humans. In fact, the thymic lobule culture system parallels the SCID-hu in vivo system, but demonstrates faster kinetics. Thus, the results from initial screening of compounds provided by this invention are more indicative of actual results in human clinical trials than results from previously-described in vitro systems.

In one embodiment, a method is provided to screen agents for potential anti-viral efficacy. The method comprises providing thymic lobules; incubating the lobules for a time and under conditions sufficient to maintain cell viability and to allow viral infection; exposing the lobules to a virus under conditions to induce infection; exposing the lobules to an anti-viral agent to be screened; and assaying for evidence of viral activity.

The agent is a potential anti-viral agent if it suppresses viral pathology relative to lobules incubated in a control sample.

The lobules obtained are thymic. Preferably, the thymic lobules are human, including but not limited to neonate and mature human. More preferably, the thymic lobules are from human fetal thymus tissues. The lobule is a relatively intact lymphoid organ subunit that contains many cell types such as thymocytes, macrophages, dendritic cells, and epithelial cells. Thus, it provides a more complex and in vivo-like environment than simpler cell cultures.

Thymic lobules are obtained by dissecting the whole thymus into thymic fragments. Each fragment contains at least one intact thymic lobule. The fragment is incubated separately under conditions that support cell viability and allow infection of the lobules by the virus. Suitable methods of cell culture known in the art can be used. In practice, a fragment is placed on top of a sterile filter laying across an absorbable gelatin sponge boat in a tissue culture plate containing support media.

Standard cell culture techniques are adequate for use in the methods described herein. Culture plates are maintained in incubation chambers at 37° C. in an atmosphere of 5% $CO_2$. Incubation periods prior to infection may range from essentially no incubation prior to infection to periods as long as the lobules can be maintained in a viable state and still retain the ability to be infected by the target virus. Typically, incubation periods range from approximately less than one day to about fourteen days. Although the optimal medium varies depending on the lobule source, the type of virus, and the length of the incubation period, the preferred medium is one which supports cell viability and allows infection of the lobules by the target virus. Preferably, the medium is Roswell Park Memorial Institute medium (RPMI-1640) supplemented with 10% fetal calf serum (FCS), glutamine, penicillin and streptomycin.

Successful maintenance of cell viability is dependent on maintenance of intact lobules and an air interface for cultured lobules. Preferably, medium is changed daily. More preferably, 1X I/S/T (insulin/selenium/transferrin, Sigma) is added as a supplement to the medium to enhance cell viability.

The methods described herein are suitable for use in screening potential therapeutic agents against a wide variety of viruses. Candidate viruses would include those which infect cells found in the thymus. Such viruses include but are not limited to human cytomegalovirus, human immunodeficiency virus (HIV), herpes simplex virus (HSV), and rubella virus. The cells found in the thymus include but are not limited to thymocytes, dendritic cells, macrophages, endothelial cells, fibroblasts, B cells, and epithelial cells. Preferably, the viruses are those which infect thymocytes or cells in the thymic stroma which are important for T cell development. More preferably, the viruses are various isolates of HIV. Suitable isolates of HIV are those which are most similar to those which infect human patients. Such isolates include but are not limited to primary isolates such as EW and infectious molecular clones such as JR-CSF, Xho, and NL4-3.

The types of anti-viral agents suitable for testing in this assay are virtually unlimited. Agents can be obtained from chemical, nutritional and biological sources. For instance, suitable chemical agents can be novel, untested classes of chemicals, as well as agonists, antagonists, or modifications of known therapeutic agents. Nutritional agents can be simple or complex, ranging from minerals to extracts from plant and animal sources. Such agents can be easily derived from plant sources including but not limited to soy, pea, and potato by-products, and from animal products such as whey or other milk byproducts. Biological agents include but are not limited to biological response modifiers (such as cytokines), antibodies, and other so-called "small molecules." Such agents can either be derived from biological sources or chemically synthesized to mimic the effect of biological response modifiers. Anti-viral agents may also include those mediating an effect through a cellular vehicle. For example, infected, uninfected, transduced, or non-transduced cells of various phenotypes (such as monocytes, macrophages, epithelial cells) may be introduced, such as by microinjection, into the lobules to assess their effect on viral replication or pathology.

The assay allows rapid screening of potential anti-viral agents, thus enabling the screening of large numbers of different agents at multiple concentrations. The therapeutic agents tested to date have been effective in this assay at concentrations in the sub-micromolar range, indicating that the assay is extremely sensitive. This is a real benefit over current animal systems which require large amounts of agents for screening. Preferably, the range of concentrations of agents used in this assay is about 0.001 µM to 5 mM. The upper range is limited by the solubility of the agent and toxicity of high concentrations of some drugs; the lower range is not necessarily limited but should be low enough to encompass a complete dose-response curve.

The lobules can be infected by any method known in the art, including but not limited to incubating the lobules in a liquid containing the virus particles for a length of time suitable to allow infection. The amount of virus used for infection (reported as infectious dose) depends on the type of virus, the method of infection, the incubation conditions of the cells, etc. The infectious dose necessary to follow the methods herein is determined empirically. Such determination is well within the skill of one in the art. A suitable infectious dose is one which allows measurement of a parameter of viral activity and/or infectivity.

In the case of HIV, virus can be added to the lobules by dripping virus-containing liquid over the top of thymic lobules being incubated on absorbable gelatin sponge boats. Preferably, however, the thymic lobules are incubated for approximately two hours in vials containing undiluted virus. This is the so-called "dip" method. In the examples described below, HIV is obtained from phytohemagglutinin (PHA)-stimulated blast cells previously infected by HIV. The "undiluted" virus is simply the supernatant derived from those cells. Infection by dipping the cells in undiluted virus appears to accelerate infection and the onset of observable HIV pathology.

The anti-viral agents to be assayed are introduced into the lobules prior to, simultaneously with, or shortly after viral infection. The time of introduction will vary according to the type of virus, the incubation conditions and the method of infection. It may be useful to test the same agent at a variety of time points to insure accurate determination of efficacy. The optimal conditions in the case of HIV are to pretreat the lobules with the agent approximately 1–2 hours before infection and to incubate the pre-treated, infected lobules in presence of the agent. After addition of the agent, the lobules are further incubated for a time sufficient to allow an assayable parameter of virus infection or pathology to occur in the control cells.

Tissue fragments are harvested and disrupted to allow the release of thymocytes and other lobule contents. Extent of viral infection is determined by assaying any suitable parameter indicative of viral replication or viral-induced pathology. These parameters include but are not limited to: viral-specific DNA, RNA, or protein production, viral-induced cytokine production, thymocyte phenotype profile as determined by FACS analysis, histological analyses, apoptotic profile, DNA quantitation, DNA fragmentation profiles, immunohistochemistry, functional assays, PCR analysis of integrated proviral DNA and 2-LTR circular viral DNA, and isolation of virus in vitro.

A positive response to the anti-viral agents is manifest when cells from the lobules treated with the agent exhibit a suppressed level of viral pathology and/or replication compared to infected, untreated controls. The extent of viral replication or pathology is determined by measuring one or more of the various parameters above.

In another embodiment, the present invention is suitable for testing hypotheses concerning mechanisms of viral infection, replication, and pathology in thymic cells. Incubated thymic lobules are infected with the virus as discussed above. Lobules can be harvested at various times after infection, and a variety of viral infection parameters can be observed. Alternatively, the virus used for infection can be specifically altered genetically, and the viral activity and replication compared to infection with native, non-altered control viruses. Use of drugs or other agents with known mechanistic targets can delineate new elements of viral pathology, thereby providing new targets for intervention through cellular therapy, gene therapy, drug therapy, or rational drug design.

The following examples are provided to illustrate but not limit the claimed invention.

EXAMPLES

Example 1

Cell Culture Techniques

Fresh human fetal thymus was obtained at 18–24 weeks gestational age and kept in sterile media at 4° C. Human fetal tissues can be obtained with informed consent from agencies such as International Institute for the Advancement of Medicine (Exton, Pa.) or Advance Bioscience Resource (Alameda, Calif.), in compliance with regulations issued by State and Federal governments. Fragments of approximately 1 mm³ were dissected from the fresh thymus. These fragments represent approximately 1–4 intact thymic lobules as judged by light microscopy. Fragments are suitable for this test if they are big enough to contain intact lobules and small enough to allow diffusion of virus and agents. Typically this is about 1 mm³.

Fragments were placed on sterile CoStar Nucleopore® filters (13 mm/0.8 μm) that lie across Gelfoam® sterile sponge boats (Upjohn) saturated in growth media. Growth media was RPMI (1640) with 10% FCS, glutamine, penicillin and streptomycin. Culture plates, typically Cell Wells™, 6-well flat bottom 35 mm polystyrene plates (Corning), were maintained in incubation chambers at 37° C. under 5% $CO_2$. Preferably, the culture medium was enriched every 48 hours by removing old medium and then dripping fresh medium over fragments. Incubation periods ranged from less than one day up to approximately 2 weeks. Typically, a majority of the cells of the lobules were viable for approximately 10 days under these culture conditions.

The number of viable thymocytes from the lobules over a two week incubation period is shown in FIG. 1. The results show that a significant loss of thymocytes occurred during culture.

Figure 2A:
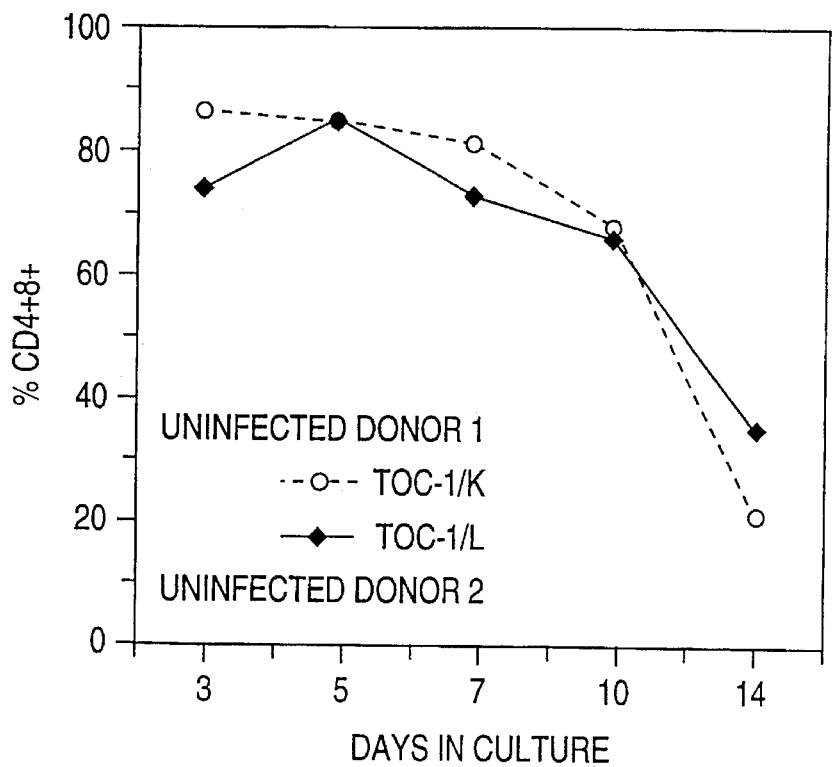
FIGS. 2(a) and (b) contain two graphs depicting (a) relative and (b) absolute numbers of CD4+/8+ cells in uninfected cultures.
Figure 2B:
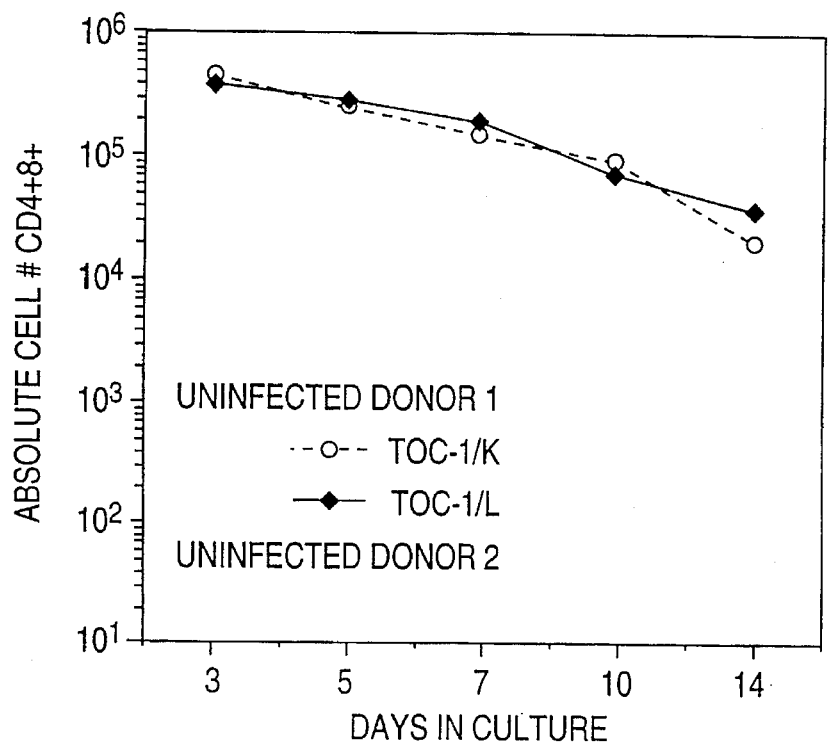
FIG. 2 is discussed in Example 1.

Relative and absolute CD4+/8+ profiles of the cells from the thymic lobule culture are shown in FIGS. 2(a) and 2(b), respectively. These figures showed a depletion in this cell population over the two-week incubation period, indicating a significant baseline of cell loss/death in this culture system.

Since viral infection can also cause cell loss/death, it was desirable to develop culture conditions that maximized thymus fragment cellularity and cell viability.

To optimize cell culture conditions, various media modifications were tested for their ability to enhance overall thymus fragment stability. The culture conditions were modified as follows:

a) variation in FCS concentrations (2–20%);

b) addition of the reducing agent 2-mercaptoethanol (2-ME to a final concentration of 50 μM);

c) addition of epidermal growth factor (EGF at 10 ng/ml);

d) addition of 1X supplement containing trace amounts of I/S/T (Sigma).

In the case of 2-ME, EGF, or I/S/T containing media, 10% FCS was used. Uninfected cultures were assayed on day 11 for cell yields, percent viability, and. CD4+/8+ distribution patterns. The results obtained are shown in Table 1. Data represent mean values averaged from three fragments cultured under identical conditions for 11 days.

These data suggest that supplementing media with 1X I/S/T helped maintain thymocyte longevity in culture, as evidenced by viability, increased representation of CD4+/8+ thymocytes and increased cell yields following 11 days culture. Varying other culture conditions did not produce any obvious growth or maintenance advantages.

TABLE 1

Effect of cell culture conditions on thymic cell viability

| Culture Condition | Cells per Fragment (×10³) | % Live Cells | % CD4+ 8– | % CD4– 8+ | % CD4+ 8+ | Absolute Number CD4+8+ |
|---|---|---|---|---|---|---|
| 2% FCS | 113 | 27 | 39 | 13 | 39 | 43000 |
| 10% FCS | 122 | 32 | 31 | 14 | 46 | 59000 |
| 20% FCS | 83 | 25 | 38 | 12 | 40 | 34000 |
| 2-ME | 99 | 27 | 47 | 11 | 32 | 34000 |
| EGF | 43 | 17 | 35 | 9 | 45 | 20000 |
| 1X I/S/T | 167 | 43 | 25 | 12 | 56 | 96000 |

The effects of different lots of FCS, vitamin supplements (GIBCO MEM additive), addition of 2-ME (50 μM) to I/S/T, and changing the growth medium every other day (qod) instead of daily (qd) were observed and are reported in Table 2.

TABLE 2

Effect of cell culture conditions on thymic cell viability

| Culture Condition | Cells Per Fragment (×10³) | % Live Cells | % CD4+8– | % CD4–8+ | % CD4+8+ |
|---|---|---|---|---|---|
| FCS#1 | 166 | 26 | 27 | 9 | 37 |
| FCS#2 | 130 | 33 | 35 | 14 | 43 |
| FCS#3 | 194 | 22 | 43 | 11 | 41 |
| FCS#1 +2-me | 108 | 24 | 44 | 10 | 37 |
| FCS#1 +vitamins | 116 | 44 | 48 | 12 | 35 |
| FCS#1 qod | 144 | 12 | 38 | 9 | 46 |

In Table 2, data represent mean values averaged from five fragments cultured under identical conditions for 12 days. Cultures were assayed on day 12 for cell yields, percent viability, and CD4+/8+ distribution patterns. Different lots of FCS had little or no effect on thymus cell viability, and the addition of 2-ME to I/S/T-supplemented medium offered no apparent advantage to culture maintenance. Vitamin supplements appeared to confer some benefits in overall cell viability at day 12. Cultures fed every other day with I/S/T-supplemented medium had fewer viable cells than cultures fed every day. Based upon these results, it is preferred that thymic lobules be maintained with I/S/T-supplemented medium that is replaced daily.

Example 2

Methods of Obtaining HIV for Infection of Thymic Lobules

PHA-activated T-cell blasts are required for preparing the HIV virus stocks. PHA blasts were either freshly prepared or frozen. Frozen cells must be thawed and put into culture media containing interleukin-2 (IL-2) at least 24 hr before HIV infection. Fresh cells are preferable to frozen cells.

PHA-activated human T-cell blasts were produced by obtaining buffy coats of human cells from a local blood bank. Cells were removed from the bag under sterile conditions and mixed with an equal volume of phosphate-buffered saline (PBS) or Hank's balanced salt solution (HBSS) with heparin (2 ml of 1000 units/ml made up in 250 ml of PBS or HBSS). Approximately 35 ml of the diluted cell suspension wad aliquoted into 50 ml conical centrifuge tubes. The cell suspension was underlayered with approximately 14 ml of Ficoll-hypaque (HISTOPAQUE®, Sigma) and centrifuged at 450 RCF (about 1400 rpm) for 30 min with the brake off. The interface cells were harvested, washed twice with PBS and counted. In some cases, the cells were resuspended in 50 ml, diluted 1:5 and counted. For. incubation, cells were resuspended at $2-3 \times 10^6$ per ml in Iscove's Modified Dulbecco's (IMDM) media containing 10% FCS, 2 mM L-glutamine, penicillin to a final concentration of 100 U/ml, streptomycin to a final concentration of 100 μg/ml and 1 μg/ml of phytohemagglutinin-P (PHA-P). Cells were incubated, maintaining a cell density of $2-3 \times 10^6$ for three days and either frozen in 10% dimethyl sulfoxide (DMSO)/FCS and stored in liquid nitrogen, or used directly in infection experiments.

When frozen PHA blasts were used, the PHA blasts were thawed and incubated overnight in medium containing 50 units/ml of IL-2 prior to infection. PHA blasts were then pelleted by centrifugation at 1000 rpm for 5 min.

The PHA blasts were infected by resuspending the blasts in virus ($10^3-10^4$ TCID$_{50}$) containing 5 μg/ml of polybrene at $1-2 \times 10^7$ cells/ml of virus. Viruses for infection must be thawed quickly at 37° C. and used as soon as possible. The starting concentration of virus inoculum was 5 ml of a stock with TCID$_{50}$ of $10^3$ or $10^4$ per $10^8$ cells. Infection was allowed to occur for about 2 hr at 37° C. After 2 hr cells were diluted up to the appropriate volume in medium containing IL-2 at 50 Units/ml at a cell density of $2-3 \times 10^6$/ml. On day 2 or 3 (depending on virus), the cells were pelleted and fresh medium was added. Starting on day 3 or 4, supernatant was collected until day 8 or 9 at 24-hr intervals, and fresh medium containing IL-2 was added. The collected supernatant was aliquoted into freezing vials labelled with the date and type of virus. An aliquot also was saved for p24 analysis by adding 1/10 volume of 10% Triton X-100 to the supernatant and storing at 4° C. until analysis. The freezing vials containing virus were frozen immediately in liquid nitrogen.

Example 3

Infection Techniques

The "standard" method of infection of thymic organ cultures involves dripping virus-containing PHA blast supernatant over the top of the organ fragment, the so-called "drip" method. In the case of thymic lobules already deposited on Gelfoam® boats as described in Example 1, the effectiveness of this method was determined.

To increase the initial infectious dose at time zero, an alternative infection protocol, the "dip" method, was developed. In the dip method, thymic lobules were incubated for approximately 2 hours in vials of undiluted virus-containing PHA blast supernatant. Dipped fragments were subsequently transferred to Gelfoam® boats for incubation.

For infectivity analysis, tissue fragments were harvested and disrupted using tissue homogenizers which allow for the release of lobule contents (thymocytes and other thymus constituents). Cells were counted and processed by: staining for flow cytometric analysis, quantitation of DNA content, immunohistochemistry, functional assays, and assessment of viral replication.

Figure 3:
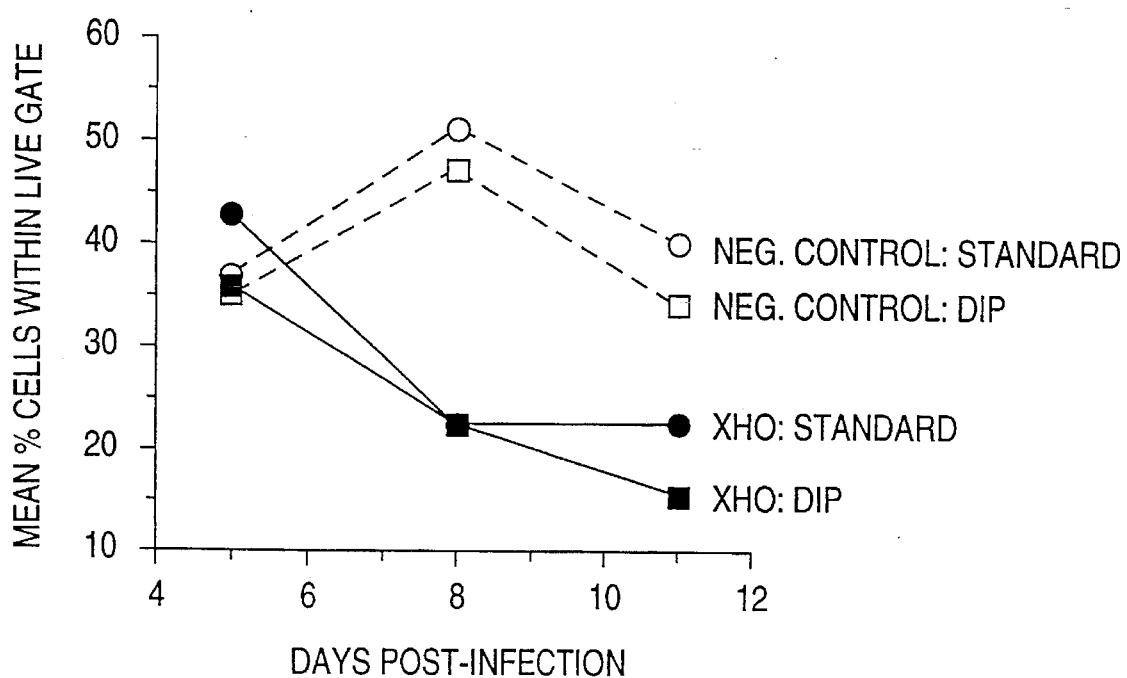
FIG. 3 is a graph depicting cell viability of cultures infected with HIV by the standard drip or dip method.
Figure 5A:
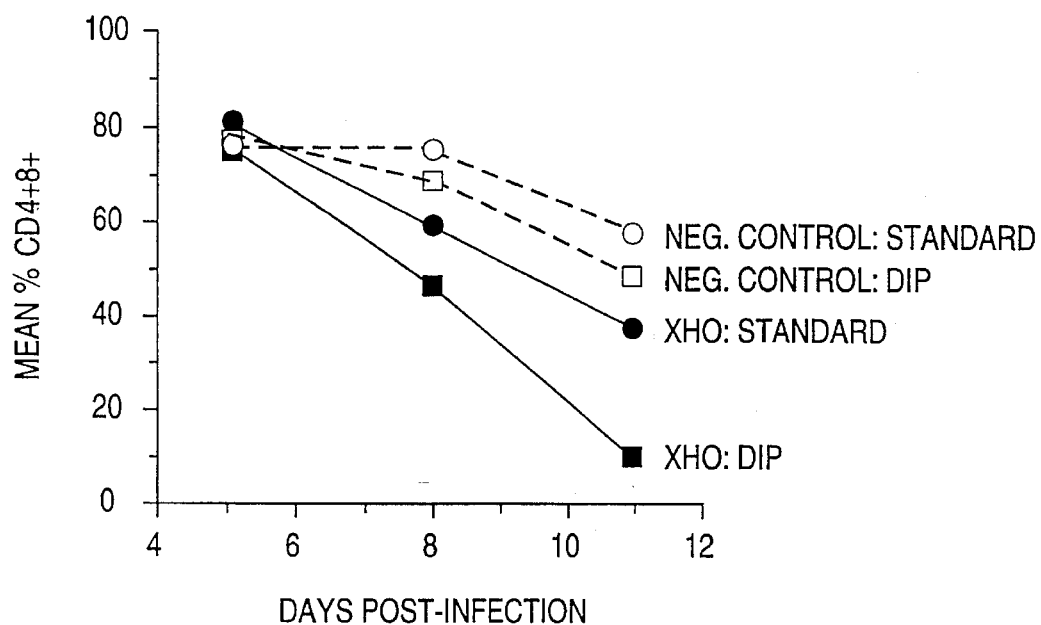
FIGS. 5(a) and (b) contain two graphs depicting the relative (a) and absolute (b) numbers of CD4+/8+ cells in cultures infected with HIV by the standard drip or dip method.
Figure 5B:
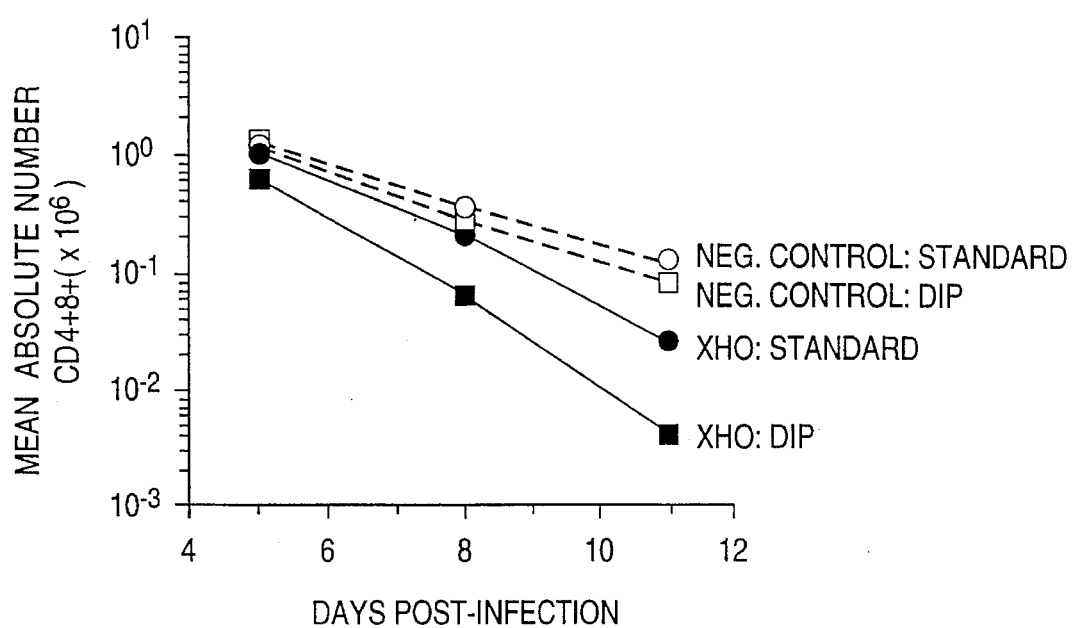
FIG. 5 is discussed in Example 3.
Figure 4:
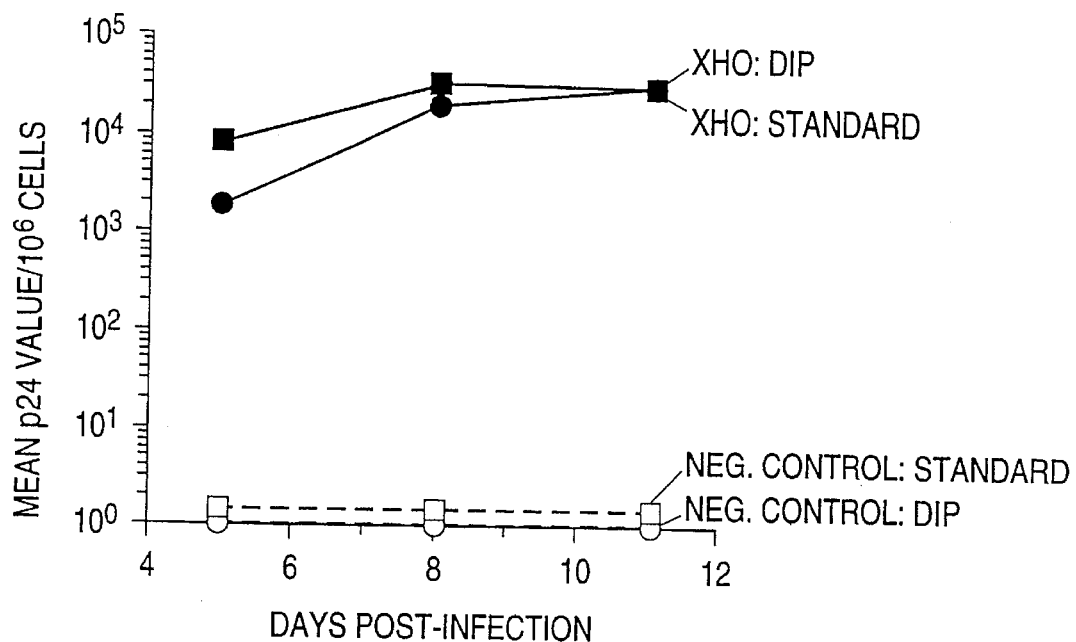
FIG. 4 is a graph depicting p24 levels in cultures infected with HIV by the standard drip or dip method.
Figure 6:
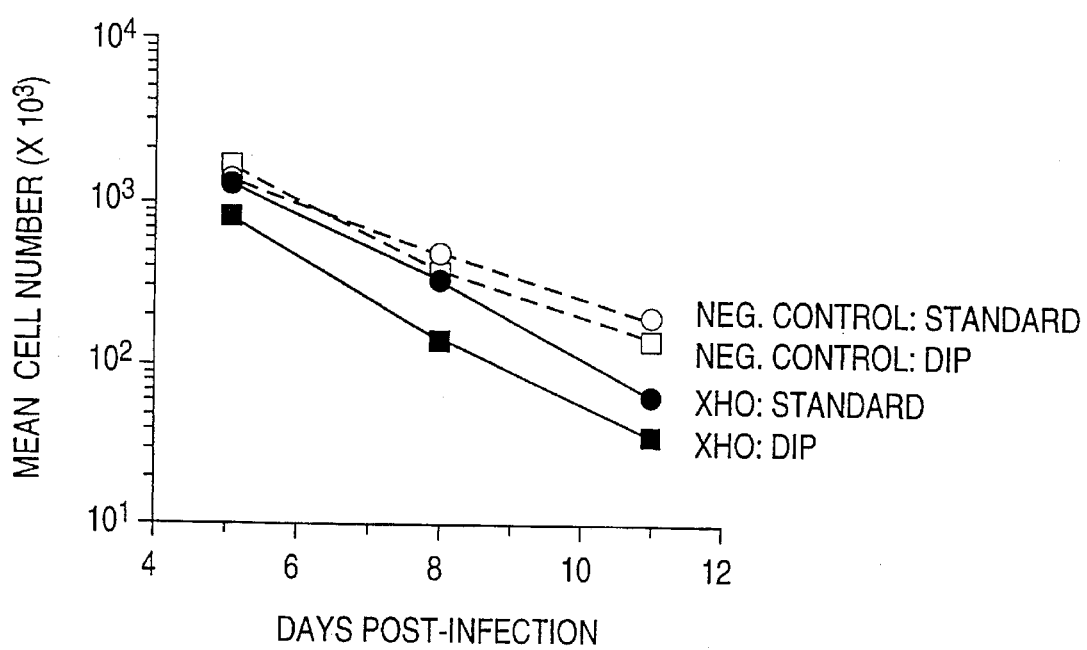
FIG. 6 is a graph depicting the number of cells in cultures infected by HIV the standard drip or dip method.

The results of these experiments are summarized in FIGS. 3–7. In general, here and as described in the HIV-infected SCID-hu mouse, inoculation of TOC with HIV (Xho in this example) resulted in decreased cell viability (FIG. 3), detectable p24 levels (FIG. 4), and decreased numbers of CD4+ CD8+ thymocytes (FIG. 5). Dip-infected TOC followed approximately the same time course of HIV (Xho)-induced cell depletion as drip-infected cells and displayed lower viability by day 11 post-infection, as shown in FIG. 3. Early in the infection, dip-infected cells produce more p24 than drip-infected cells; by 11 days post-infection, however, p24 levels were the same for cells from lobules infected by either method (FIG. 4).

HIV p24 antigen was determined using a commercially available p24 ELISA kit (DuPont) according to the manufacturer's instructions. The results are presented as pg/$10^6$ cells.

Figure 7:
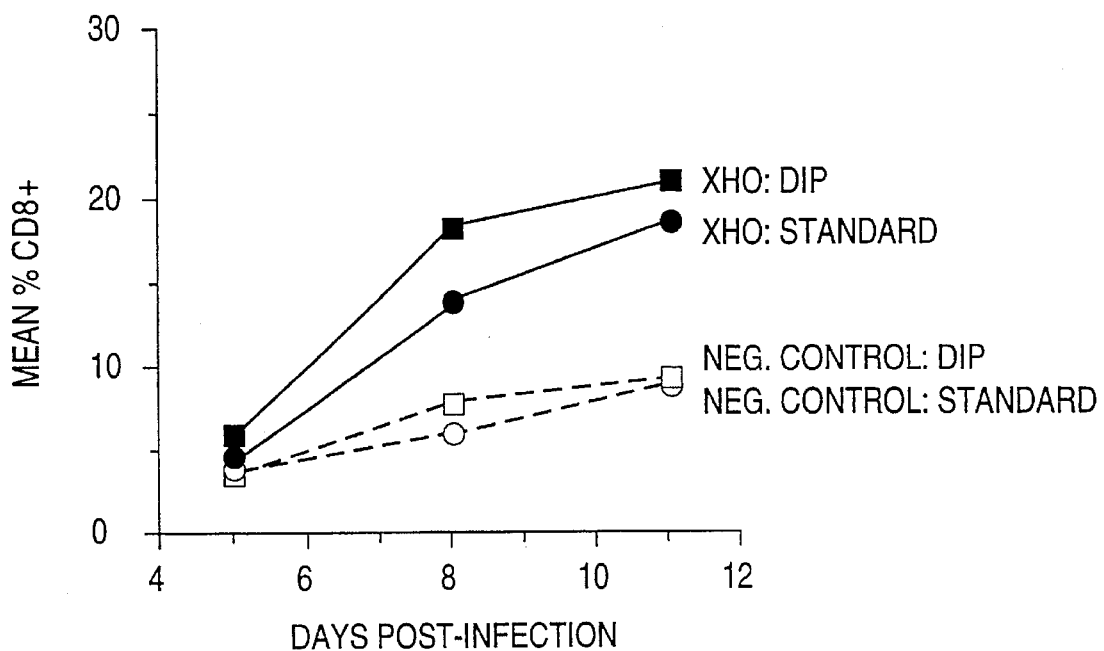
FIG. 7 is a graph depicting the relative number of CD8+ cells in cultures that have been infected with HIV by the standard drip or dip method.

Dip-infected TOC showed a greater decrease in the CD4+ 8+ population (FIGS. 5(a) and (b)) and displayed a lower cellularity (FIG. 6) than drip-infected lobules. The relative population of CD8+ cells was higher in dip-infected lobules than in drip-infected lobules, as shown in FIG. 7. Thus, the dip method of infection appeared to increase the initial infectious dose and to accelerate the spread of infection and the onset of pathology compared to the drip method.

Example 4

Pathology of HIV in the System

Figure 8:
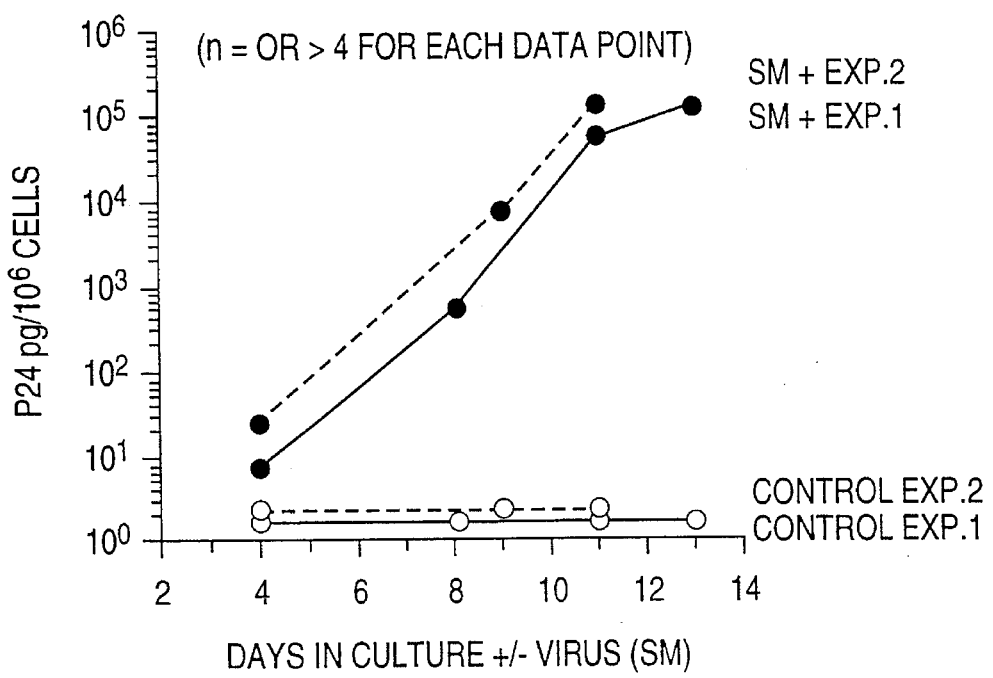
FIG. 8 is a graph depicting p24 levels of HIV-infected cultures over time.
Figure 9A:
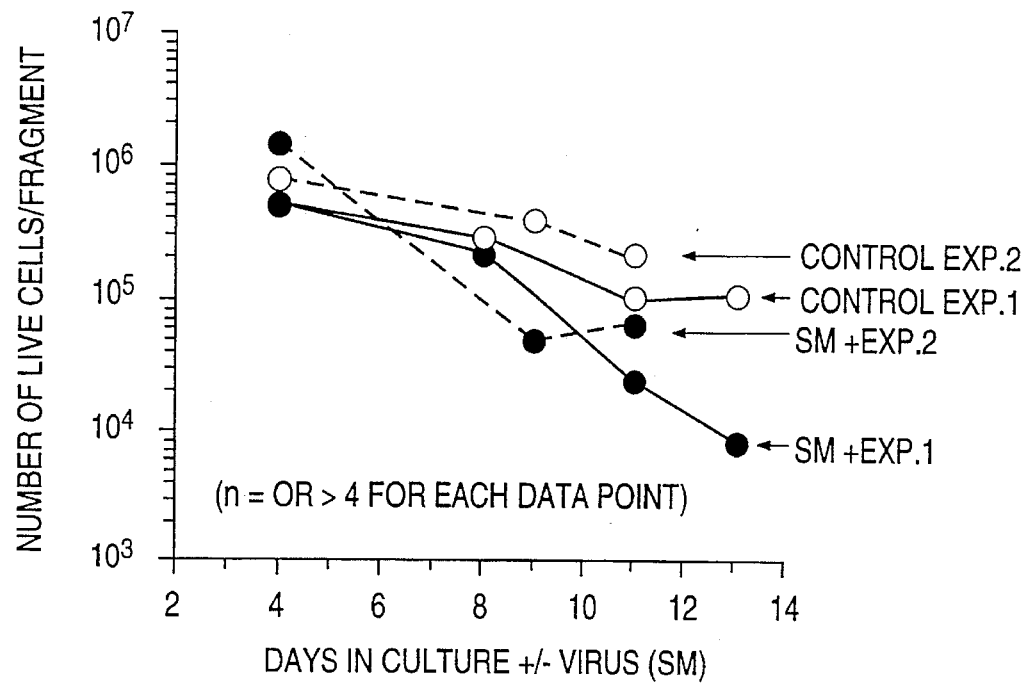
FIGS. 9(a) and (b) contain graphs depicting (a) increased cell death and (b) decreased cellularity per thymus fragment in HIV-infected cultures.
Figure 9B:
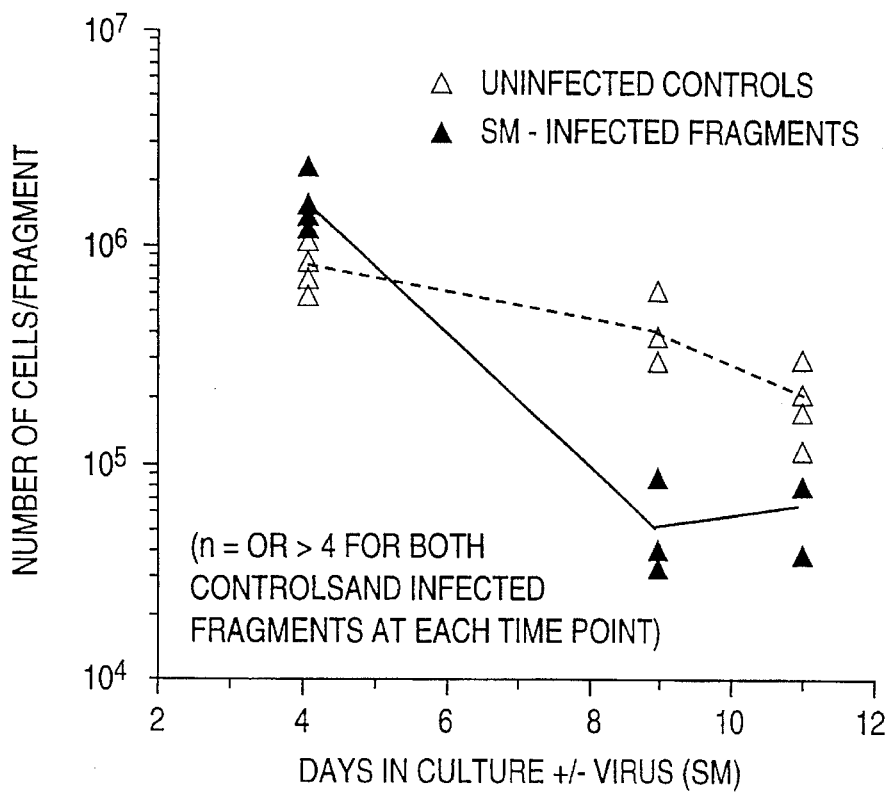
FIG. 9 is discussed in Example 4.
Figure 10A:
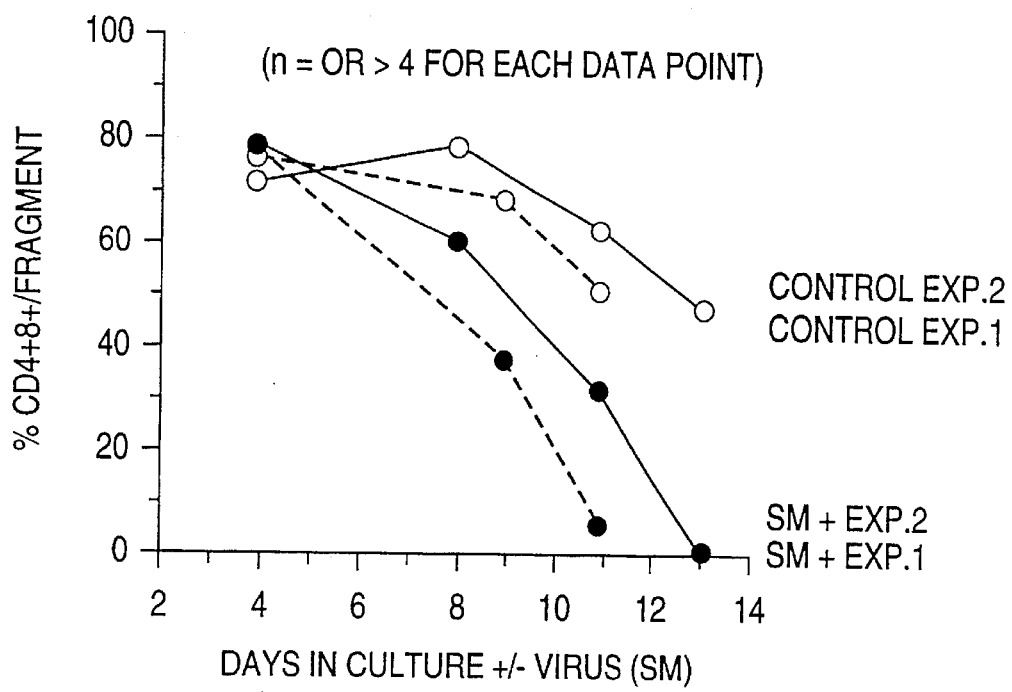
FIGS. 10(a), (b), (c) and (d) contain a series of graphs depicting in (a) and (c) relative and in (b) and (d) absolute numbers numbers of viable CD4+/8+ cells in HIV infected cultures.
Figure 10B:
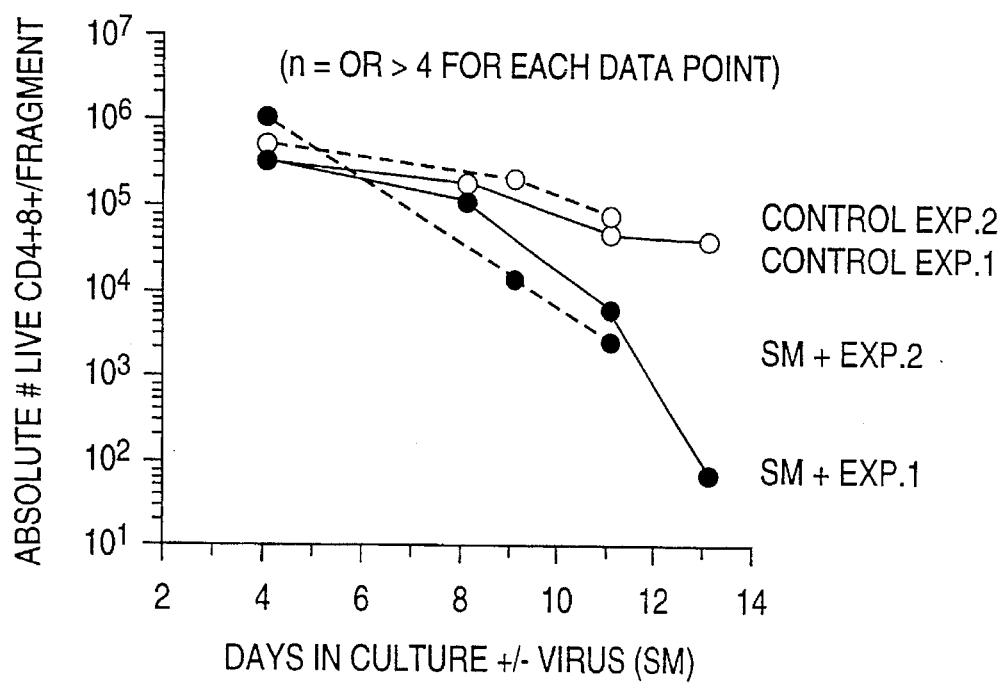
FIG. 10 is discussed in Example 4.
Figure 10C:
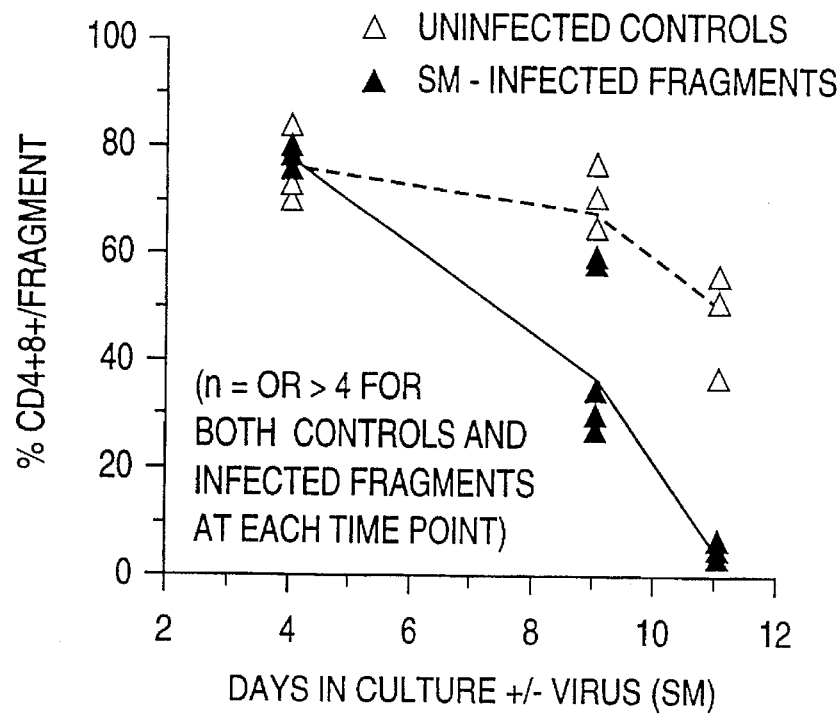
Figure 10D:
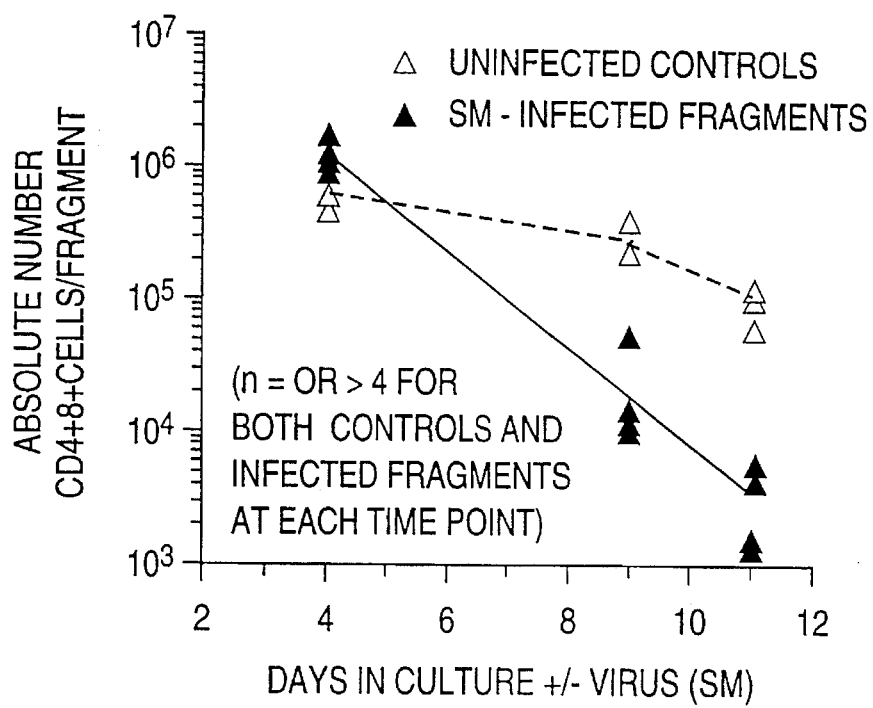
Figure 11A:
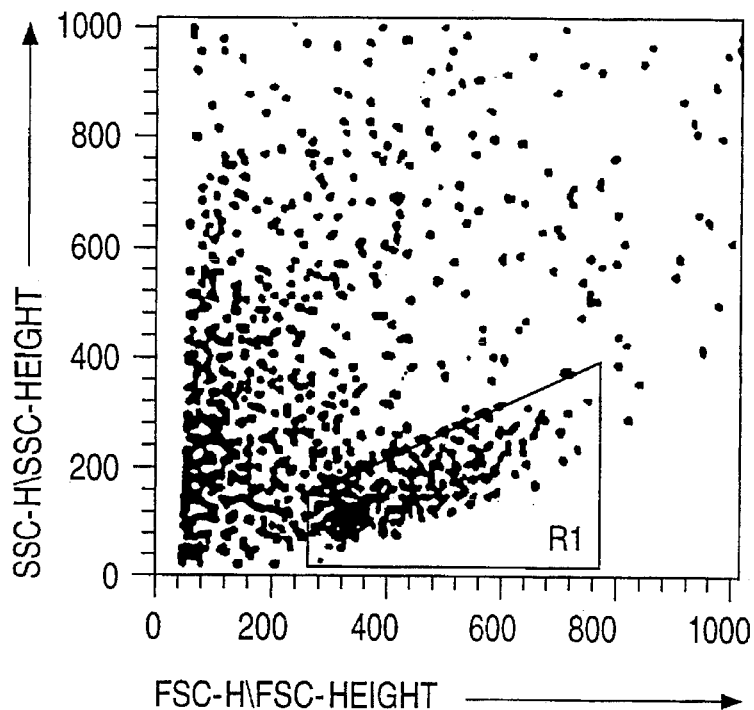
FIG. 11 is a series of graphs depicting fluorescence activated cell sorter (FACS) analysis of HIV-infected cultures.
Figure 11B:
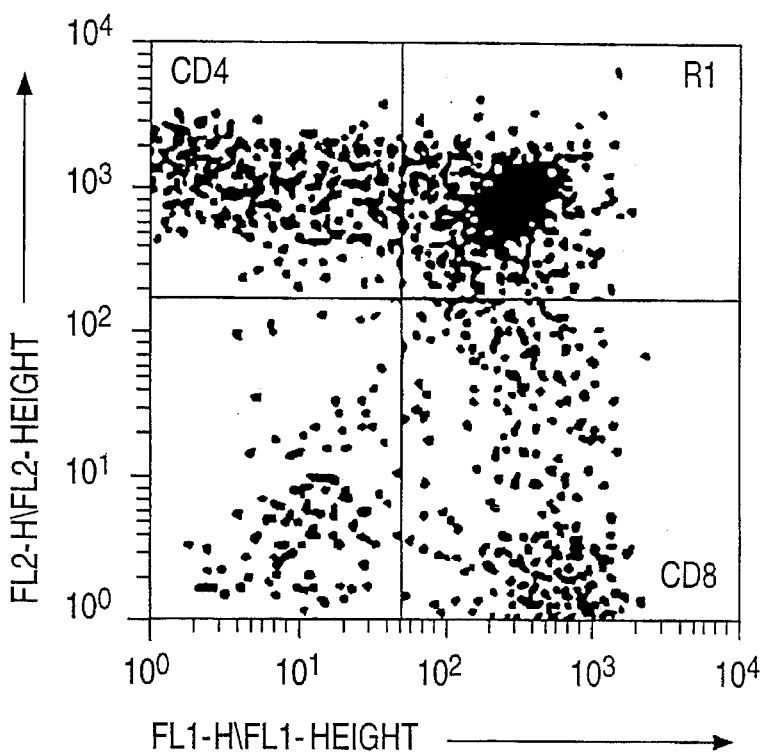
Figure 11C:
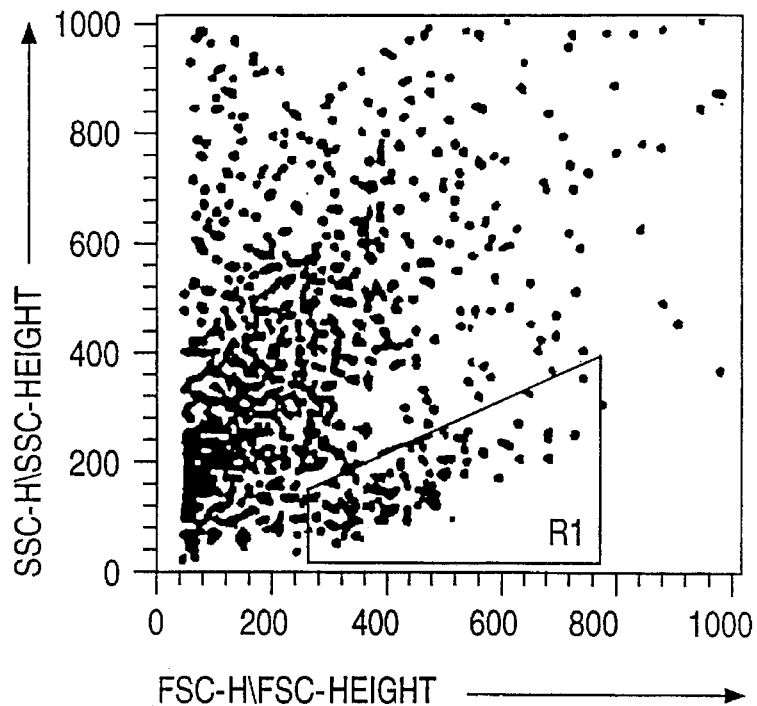
Figure 11D:
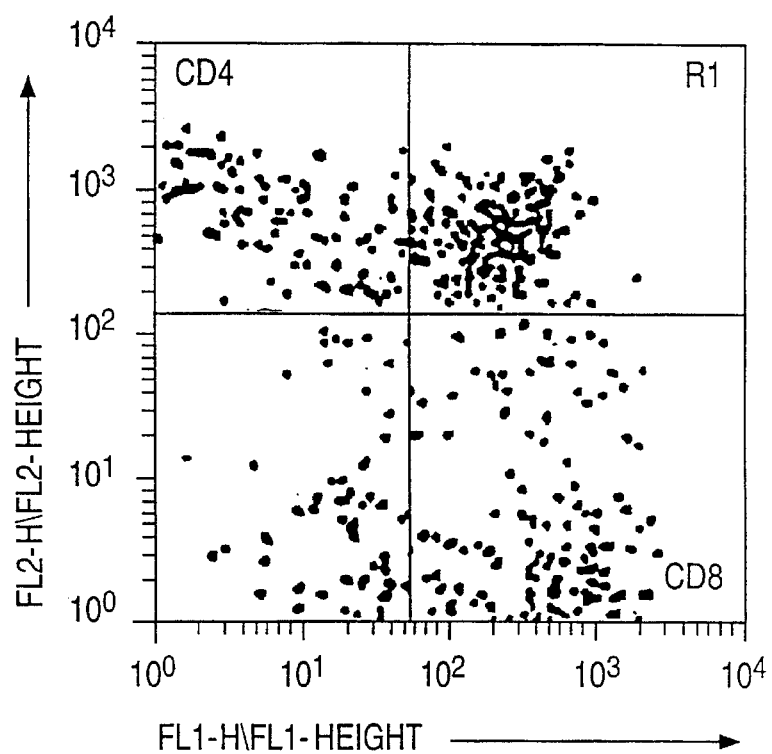

Infection by HIV (SM isolate) established that the thymic lobule culture displayed typical indices of HIV pathology. TOCs were infected by the drip method as described in Example 3. Cells from lobules were harvested at varying times post-infection. FIG. 8 shows that p24 production increased significantly over the uninfected controls. Increased cell death and decreased cellularity compared to uninfected controls is shown in FIGS. 9(a) and (b) respectively. Cell death and decreased cellularity are determined by decreased representation of cells with a high forward scatter/low side scatter profile on FACS analysis. Time-dependent depletion in the relative and absolute number of CD4+8+ thymocytes is shown in FIG. 10. The results indicate that the thymic lobule culture system displayed parameters associated with viral infection.

FACS analyses of infected cells from the lobules are shown in FIG. 11. HIV (Xho strain) infected thymic lobules (lower panel) had a lower cell viability (left panel) (as determined by decreased representation of cells with a high forward scatter/low side scatter profile, typical of live cells) and CD4+8+ population than uninfected controls (upper panels).

Example 5

Comparison of Infectivity Parameters of Different Strains of HIV

To determine if infection of the thymic organ system is reflective of in vivo infectivity, Xho, NL4-3, EW, and RIP7 HIV isolates were tested. The isolates were obtained as described in Example 2. Infection was carried out by the dip method described in Example 3. The results are shown in Table 3. Data are mean values averaged from 6 fragments cultured under identical conditions for 8 days.

The pathogenic effects of the Xho, NL4-3, and EW HIV isolates were similar, indicating that the thymic lobule culture system can be used for a variety of viral strains, thus expanding its applicability. In contrast, the RIP7 strain, which grows well in PHA blasts in vitro and does not appear to replicate in SCID-hu Thy/Liv mice, did not grow well in the thymic lobule culture system. These data, taken together, suggest that the thymic lobule culture system more closely reflects the in vivo SCID-hu mouse system.

Example 6

Assay of Therapeutic Agents

To determine whether the cell culture system described in Example 1 was effective as an in vitro model for screening potential anti-viral agents, known therapeutic agents were tested for their ability to inhibit viral infection. The virus used was HIV strain Xho. The known drugs were azidothymidine (AZT) and 2',3'-dideoxyinosine (ddI), both of which suppress HIV infection in humans.

Figure 12:
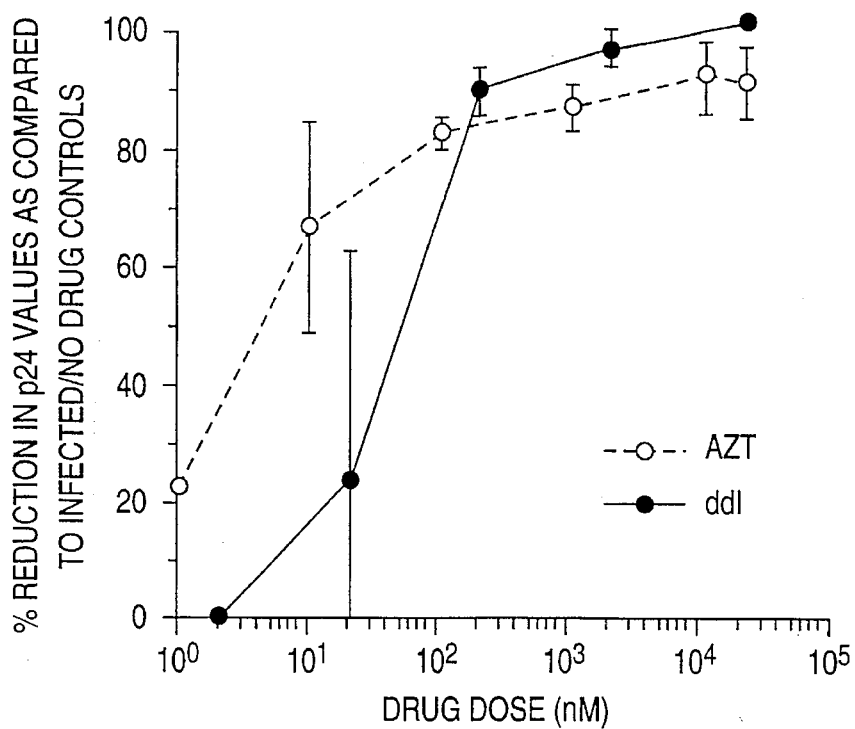
FIG. 12 is a graph depicting p24 levels in HIV-infected cultures treated with azidothymidine (AZT) or dideoxyinosine (ddI).
Figure 14:
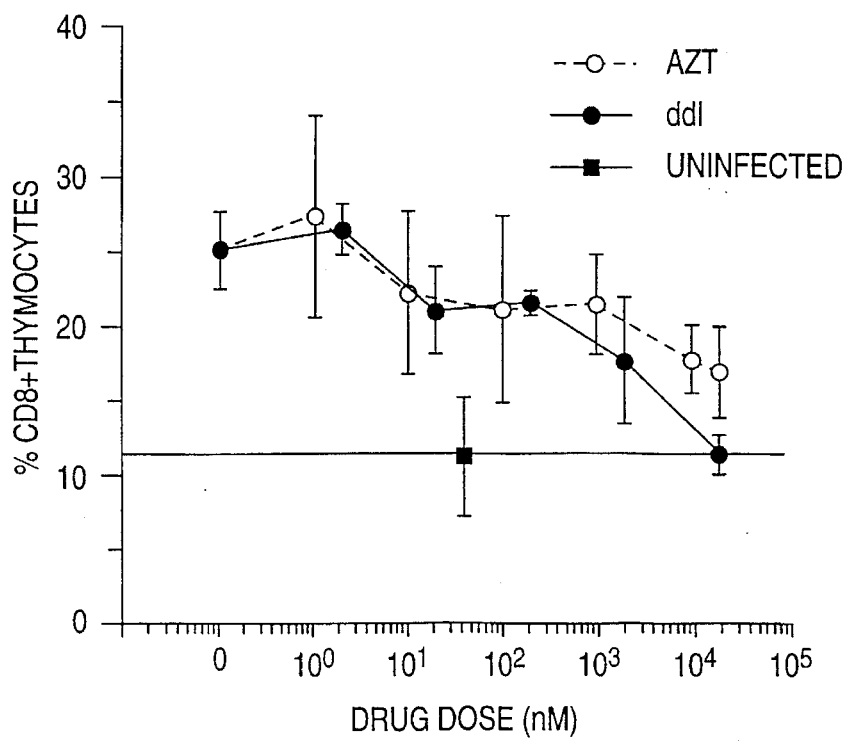
FIG. 14 is a graph depicting relative numbers of CD8+ cells in HIV-infected cultures treated with AZT or ddi.
Figure 13A:
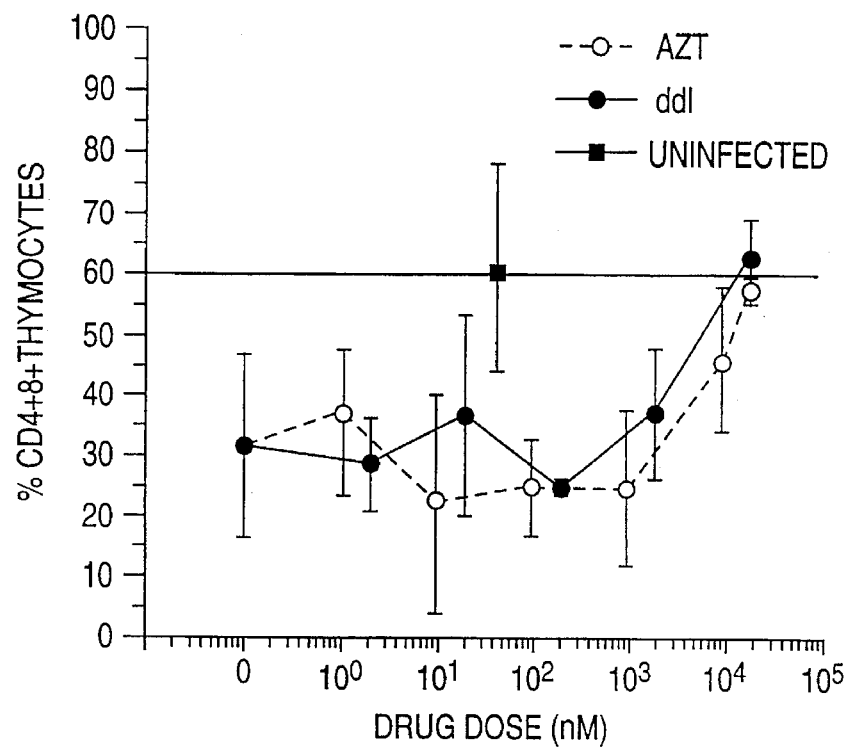
FIGS. 13(a) and (b) contain two graphs depicting, (a) relative and (b) absolute numbers of viable CD4+/8+ cells in HIV-infected cultures treated with AZT or ddi.
Figure 13B:
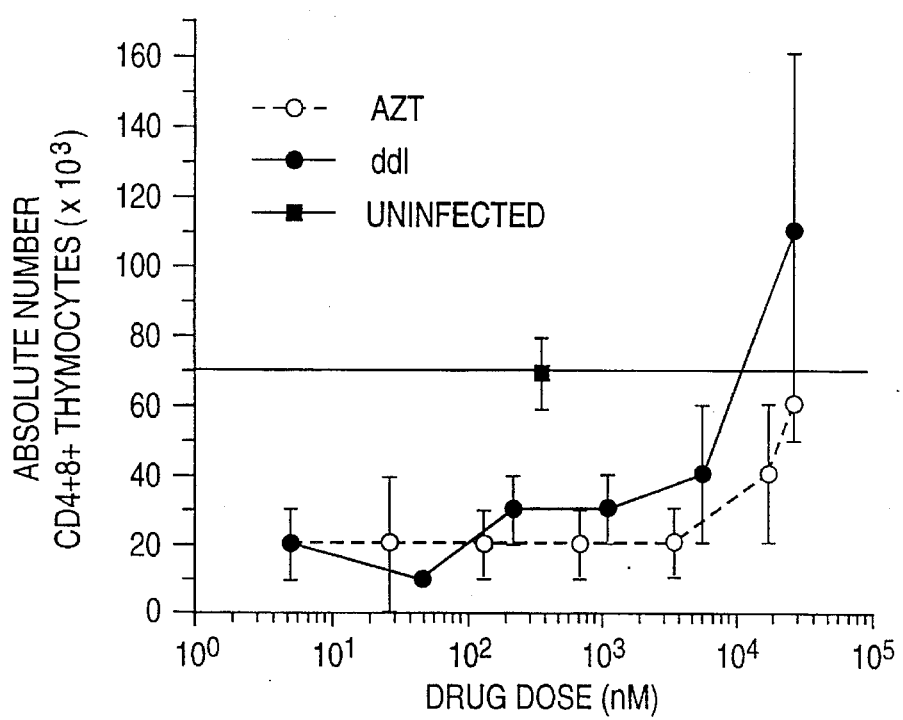
FIG. 13 is discussed in Example 6.

Varying amounts of AZT or ddI were added to lobules which had been infected with the HIV Xho strain by the dip method as described in Example 3. In this experiment, the growth medium contained no I/T/S supplement, as described in Example 1. Lobules were harvested at various days post-infection and their cellular contents were assayed for various parameters of infection and pathology. One culture of control lobules culture of control lobules was not infected and received no therapeutic agent. Parameters assayed were as follows: a) cell viability; b) p24 content; and c) CD4+/8+ profiles. The results are shown in Table 4 and FIGS. 12–14.

The data indicate that both ddI and AZT inhibit viral replication in the thymic lobule culture system, even when administered at sub-micromolar levels (Table 4). AZT treatment was inhibitory even at extremely low doses (0.001–0.01 μM), yet doses as high as 20 μM failed to completely block viral replication (Table 4 and FIGS. 12–14). In contrast, ddI displayed a nearly linear inhibition of viral replication as drug doses increased above the 2 μM range, and complete blockage was seen at 20 μM (Table 4 and FIGS. 12–14).

A comparison between the percent reduction in p24 values seen at various doses of AZT and ddI for three separate experiments is shown in Table 5.

The results presented in Table 5 suggest that the thymic lobule culture system can generate reproducible results reflecting the efficacy of both AZT and ddI in blocking HIV replication.

TABLE 3

| Days post-infection | Virus | number of fragments | p24 pg per $10^6$ cells | Cells per fragment $\times 10^3$ | Percent Live | CD4 to CD8 ratio | percent CD4+8− | percent CD4−8+ | percent CD4+8+ | Abs. # 4+8+ $\times 10^4$ |
|---|---|---|---|---|---|---|---|---|---|---|
| 8 | none | 6 | 0 | 610 | 70 | 1.60 | 7 | 5 | 86 | 53 |
| 8 | XHO | 6 | 45707 | 93 | 37 | 0.69 | 13 | 19 | 53 | 5 |
| 8 | NL4-3 | 6 | 42229 | 83 | 25 | 0.60 | 12 | 21 | 48 | 4 |
| 8 | EW | 6 | 11917 | 343 | 62 | 0.75 | 5 | 8 | 83 | 29 |
| 8 | RIP7 | 6 | 195 | 587 | 69 | 1.32 | 5 | 4 | 89 | 52 |

TABLE 4

Dose response of ddI and AZT (Xho Strain)

| Days Post-Infection | Virus (XHO) | Drug/Dose (μM) | No. of Fragments | Cells Per Fragment $\times 10^3$ | Percet Live Cells | % Reduction in p24 Value | % CD4+8− | % CD4−8+ | % CD4+8+ | Abs. # 4+8+ $\times 10^4$ |
|---|---|---|---|---|---|---|---|---|---|---|
| 9 | − | — | 14 | 211 | 33 | 100 | 21 | 11 | 61 | 7 |
| 9 | + | — | 14 | 111 | 14 | 0 | 24 | 25 | 32 | 2 |
| 9 | + | ddI 0.002 | 9 | 137 | 20 | 0 | 23 | 27 | 28 | 1 |
| 9 | + | ddI 0.020 | 13 | 149 | 18 | 23 | 24 | 21 | 36 | 3 |

TABLE 4-continued

Dose response of ddI and AZT (Xho Strain)

| Days Post-Infection | Virus (XHO) | Drug/Dose (μM) | No. of Fragments | Cells Per Fragment ×10³ | Percet Live Cells | % Reduction in p24 Value | % CD4+8− | % CD4−8+ | % CD4+8+ | Abs. # 4+8+ ×10⁴ |
|---|---|---|---|---|---|---|---|---|---|---|
| 9 | + | ddI 0.200 | 4 | 112 | 16 | 89 | 31 | 22 | 24 | 3 |
| 9 | + | ddI 2.000 | 4 | 108 | 24 | 96 | 28 | 18 | 37 | 4 |
| 9 | + | ddI 20.000 | 4 | 170 | 21 | 100 | 19 | 11 | 63 | 11 |
| 9 | + | AZT 0.001 | 5 | 107 | 16 | 22 | 16 | 27 | 37 | 2 |
| 9 | + | AZT 0.010 | 9 | 110 | 15 | 66 | 27 | 22 | 22 | 2 |
| 9 | + | AZT 0.100 | 4 | 99 | 23 | 82 | 26 | 21 | 24 | 2 |
| 9 | + | AZT 1.000 | 4 | 91 | 20 | 86 | 32 | 22 | 24 | 2 |
| 9 | + | AZT 10.000 | 9 | 112 | 22 | 91 | 25 | 18 | 46 | 4 |
| 9 | + | AZT 20.000 | 5 | 167 | 17 | 90 | 18 | 17 | 58 | 6 |

TABLE 5

Effect of ddI and AZT on Reduction of p24 Expression (Xho Strain)

| Drug/Dose (μM) | Percent Reduction in p24 Values as Compared to Controls Experiment #1 (terminated at day 8) | Percent Reduction in p24 Values as Compared to Controls Experiment #2 (terminated at day 9) | Percent Reduction in p24 Values as Compared to Controls Experiment #3 (terminated at day 9) |
|---|---|---|---|
| none | 0% | 0% | 0% |
| ddI 0.002 | n.d. | n.d. | 0% |
| ddI 0.020 | n.d. | 49% | 0% |
| ddI 0.200 | 82% | 89% | n.d. |
| ddI 20.000 | 99% | 96% | n.d. |
| ddI 20.000 | 100% | 100% | n.d. |
| AZT 0.001 | n.d. | n.d. | 22% |
| AZT 0.010 | n.d. | 73% | 54% |
| AZT 0.100 | 89% | 82% | n.d. |
| AZT 1.000 | 96% | 86% | n.d. |
| AZT 10.000 | 93% | 94% | 87% |
| AZT 20.000 | n.d. | n.d. | 90% |

Figure 15:
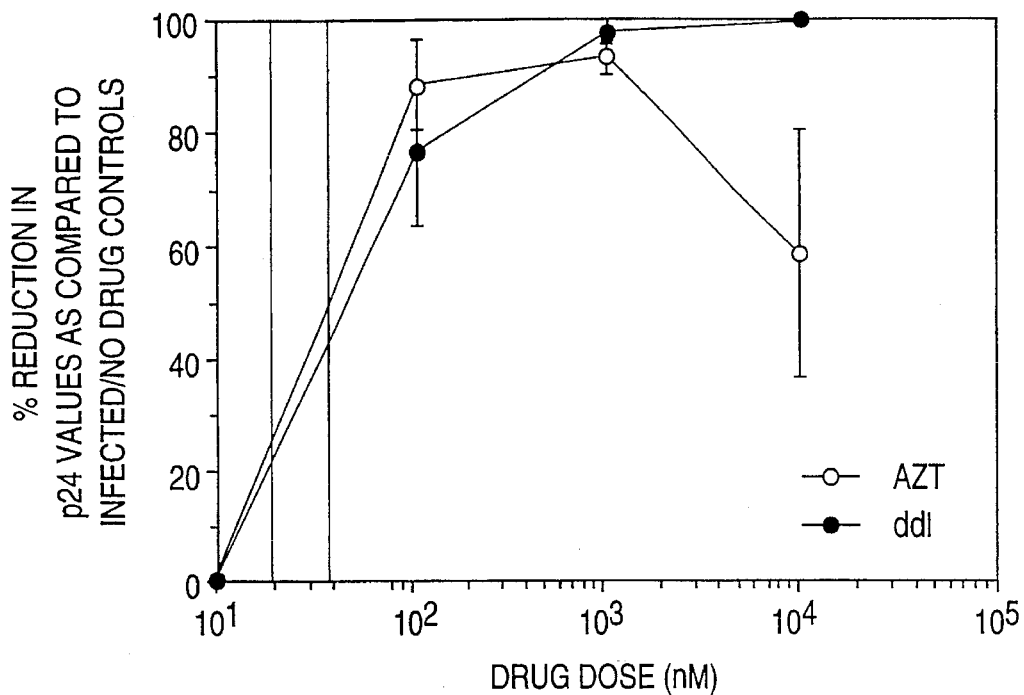
FIG. 15 is a graph depicting p24 levels in HIV-infected cultures (EW strain) treated with AZT or ddI.
Figure 16:
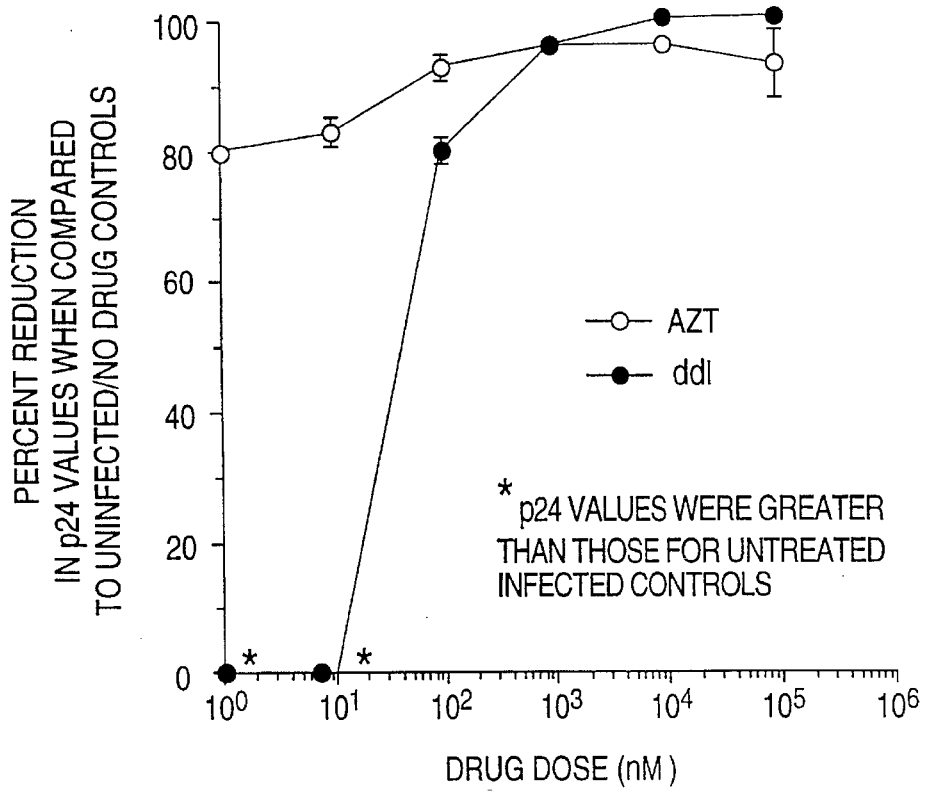
FIG. 16 is a graph depicting p24 levels in HIV-infected cultures (NL4-3 strain) treated with AZT or ddI.

Two additional strains of HIV (EW and NL4-3) were also tested. The infection method, culture conditions, and controls were the same as described for the Xho strain. Percent reduction in p24 levels for various doses of AZT and ddI is shown in FIGS. 15 (EW strain) and 16 (NL4-3 strain). Several infection parameters from these dose response experiments are summarized in Tables 6 (EW strain) and 7 (NL4-3 strain). The results demonstrate that the thymic lobule culture system reflects the in vivo efficacy of both AZT and ddI in blocking replication of a variety of HIV strains.

It was also found that the effects of ddI and AZT more closely approximate those seen in vivo (i.e., with SCID-hu Thy/Liv mice or humans) than in vitro (i.e., PHA-activated peripheral blood mononuclear cells (PBMC)). In contrast to the general observation in vitro, where ddI appears to be less effective than AZT in blocking HIV infection, both AZT and ddI appeared to have comparable efficacies in the thymic lobule culture system. These observations suggest that the thymic lobule culture assay system more closely parallels the in vivo SCID-hu Thy/Liv model than other in vitro cell assay systems for testing drug efficacy in blocking HIV infection.

TABLE 6a

Dose response of ddI and AZT (EW strain)

| Day | Virus | AZT μM | ddI μM | No. of lobes | Cells Per Fragment ×10³ | p24 pg/10⁶ cells | p24 % HIV + no drug | ratio CD 4 to 8 | cells % live | Abs # 4+8+ ×10⁶ | % CD4+ | % CD 4+8+ | % CD 8+ |
|---|---|---|---|---|---|---|---|---|---|---|---|---|---|
| 9 | NC | 0 | 0 | 3 | 283 | 0 | 0 | 3.56 | 33 | 0.212 | 15.67 | 74.57 | 4.38 |
| 9 | EW | 0 | 0 | 3 | 207 | 21980 | 1 | 0.79 | 55 | 0.169 | 6.83 | 81.65 | 9.09 |
| 9 | EW | 0 | 0.01 | 3 | 73 | 34267 | 1.559 | 1.03 | 19 | 0.042 | 13.57 | 53.94 | 14.57 |
| 9 | EW | 0 | 0.1 | 3 | 186 | 4993 | 0.227 | 1.86 | 44 | 0.261 | 12.71 | 75.69 | 6.71 |
| 9 | EW | 0 | 1 | 3 | 413 | 409 | 0.019 | 2.97 | 44 | 0.343 | 10.52 | 82.78 | 3.56 |
| 9 | EW | 0 | 10 | 3 | 233 | 0 | 0 | 1.98 | 44 | 0.196 | 9.53 | 83.06 | 4.70 |
| 9 | EW | 0.01 | 0 | 3 | 140 | 22000 | 1.002 | 0.86 | 45 | 0.109 | 8.06 | 77.43 | 9.43 |
| 9 | EW | 0.1 | 0 | 3 | 280 | 2473 | 0.113 | 1.47 | 64 | 0.234 | 8.56 | 83.29 | 5.88 |
| 9 | EW | 1 | 0 | 3 | 387 | 1373 | 0.063 | 1.66 | 48 | 0.332 | 6.53 | 86.37 | 3.93 |
| 9 | EW | 10 | 0 | 3 | 173 | 8900 | 0.406 | 2.03 | 36 | 0.124 | 15.57 | 68.99 | 7.44 |

TABLE 6b

Dose response of ddI and AZT (EW strain)

| Day | Virus | AZT μM | ddI μM | No. of lobes | Cells Per* Fragment ×10³ | p24* pg/10⁶ cells | p24 % HIV* + no drug | ratio* CD 4 to 8 | cells* % live | Abs #* 4+8+ ×10⁶ | %* CD4+ | %* CD 4+8+ | %* CD 8+ |
|---|---|---|---|---|---|---|---|---|---|---|---|---|---|
| 9 | NC | 0 | 0 | 3 | 188 | 0 | 0 | 0.57 | 9 | 0.14 | 3.33 | 4.20 | 0.41 |
| 9 | EW | 0 | 0 | 3 | 12 | 3451 | 0.157 | 0.17 | 6 | 0.02 | 1.74 | 5.54 | 3.61 |
| 9 | EW | 0 | 0.01 | 3 | 23 | 6768.6 | 0.3078 | 0.37 | 14 | 0.03 | 2.28 | 18.68 | 6.13 |
| 9 | EW | 0 | 0.1 | 3 | 188 | 2815.1 | 0.128 | 0.16 | 3 | 0.16 | 6.08 | 10.07 | 2.89 |
| 9 | EW | 0 | 1 | 3 | 201 | 272.71 | 0.023 | 0.42 | 19 | 0.17 | 1.13 | 2.70 | 0.25 |
| 9 | EW | 0 | 10 | 4 | 82 | 0 | 0 | 0.34 | 25 | 0.09 | 4.68 | 21.40 | 6.20 |
| 9 | EW | 0.01 | 0 | 3 | 34 | 2828.4 | 0.128 | 0.66 | 19 | 0.19 | 3.93 | 19.09 | 6.81 |
| 9 | EW | 0.1 | 0 | 3 | 106 | 1651.7 | 0.075 | 0.71 | 18 | 0.10 | 2.07 | 2.87 | 0.38 |
| 9 | EW | 1 | 0 | 3 | 23 | 721.76 | 0.033 | 0.57 | 13 | 0.02 | 0.65 | 1.41 | 1.05 |
| 9 | EW | 10 | 0 | 3 | 100 | 4902.9 | 0.223 | 0.27 | 19 | 0.10 | 2.31 | 8.95 | 4.13 |

*These values represent standard deviations of corresponding rows in Table 6a.

TABLE 7a

Dose response of ddI and AZT (NL4-3 strain)

| Day | Virus | AZT μM | ddI μM | No. of lobes | Cells Per Fragment ×10³ | p24 pg/10⁶ cells | p24 % HIV + no drug | ratio CD 4 to 8 | cells % live | Abs # 4+8+ ×10⁶ | % CD4+ | % CD 4+8+ | % CD 8+ |
|---|---|---|---|---|---|---|---|---|---|---|---|---|---|
| 8 | NL4-3 | 0 | 0 | 4 | 141 | 0 | 0 | 1.68 | 36 | 0.117 | 9.62 | 81.53 | 5.57 |
| 8 | NL4-3 | 0 | 0 | 5* | 36 | 24644 | 1 | 0.80 | 14 | 0.016 | 17.40 | 42.69 | 21.84 |
| 8 | NL4-3 | 0 | 0.1 | 5 | 116 | 5001 | 0.203 | 2.01 | 36 | 0.081 | 16.25 | 69.93 | 8.31 |
| 8 | NL4-3 | 0 | 1 | 5 | 142 | 907 | 0.037 | 1.50 | 49 | 0.119 | 7.79 | 83.96 | 5.21 |
| 8 | NLA-3 | 0 | 10 | 5 | 102 | 61 | 0.002 | 2.41 | 42 | 0.079 | 13.60 | 77.94 | 5.53 |
| 8 | NLA-3 | 0 | 100 | 5 | 195 | 17 | 0 | 3.13 | 42 | 0.153 | 13.92 | 78.33 | 4.57 |
| 8 | NLA-3 | 0.1 | 0 | 5 | 71 | 1732 | 0.071 | 1.59 | 41 | 0.058 | 10.44 | 80.05 | 6.81 |
| 8 | NL4-3 | 1 | 0 | 5 | 179 | 1007 | 0.041 | 1.85 | 52 | 0.153 | 8.60 | 84.57 | 4.56 |
| 8 | NL4-3 | 10 | 0 | 5 | 142 | 978 | 0.041 | 2.36 | 35 | 0.111 | 13.36 | 77.32 | 5.72 |
| 8 | NL4-3 | 100 | 0 | 5 | 83 | 1627 | 0.066 | 1.77 | 24 | 0.051 | 22.85 | 58.97 | 12.89 |

*Except p24 data is only 3 lobes.

TABLE 7b

Dose response of ddI and AZT (NL4-3 strain)

| Day | Virus | AZT μM | ddI μM | No. of lobes | Cells Per* Fragment ×10³ | p24* pg/10⁶ cells | p24 % HIV* + no drug | ratio* CD 4 to 8 | cells* % live | Abs #* 4+8+ ×10⁶ | %* CD4+ | %* CD 4+8+ | %* CD 8+ |
|---|---|---|---|---|---|---|---|---|---|---|---|---|---|
| 8 | NC | 0 | 0 | 4 | 55 | 0 | 0.00 | 0.49 | 6 | 0.05 | 4.34 | 5.82 | 0.89 |
| 8 | NL4-3 | 0 | 0 | 5* | 12 | 7377 | 0.30 | 0.08 | 3 | 0.01 | 3.67 | 13.85 | 4.17 |
| 8 | NL4-3 | 0 | 0.1 | 5 | 63 | 415 | 0.02 | 0.52 | 6 | 0.04 | 2.53 | 2.57 | 1.44 |
| 8 | NL4-3 | 0 | 1 | 5 | 18 | 343 | 0.01 | 0.05 | 8 | 0.02 | 0.45 | 1.51 | 0.40 |
| 8 | NL4-3 | 0 | 10 | 5 | 18 | 35 | 0.00 | 1.05 | 7 | 0.02 | 6.50 | 7.94 | 0.42 |
| 8 | NL4-3 | 0 | 100 | 5 | 102 | 15 | 0.00 | 0.88 | 3 | 0.08 | 1.86 | 0.97 | 0.72 |
| 8 | NL4-3 | 0.1 | 0 | 5 | 39 | 369 | 0.02 | 0.33 | 15 | 0.03 | 0.39 | 3.03 | 1.87 |
| 8 | NL4-3 | 1 | 0 | 5 | 47 | 181 | 0.01 | 0.42 | 7 | 0.05 | 3.03 | 3.81 | 0.86 |
| 8 | NL4-3 | 10 | 0 | 5 | 94 | 333 | 0.01 | 0.32 | 2 | 0.07 | 0.54 | 0.44 | 0.63 |

TABLE 7b-continued

Dose response of ddI and AZT (NL4-3 strain)

| Day | Virus | AZT μM | ddI μM | No. of lobes | Cells Per* Fragment ×10³ | p24* pg/10⁶ cells | p24 % HIV* + no drug | ratio* CD 4 to 8 | cells* % live | Abs #* 4+8+ ×10⁶ | %* CD4+ | %* CD 4+8+ | %* CD 8+ |
|---|---|---|---|---|---|---|---|---|---|---|---|---|---|
| 8 | NL4-3 | 100 | 0 | 5 | 62 | 1323 | 0.05 | 0.12 | 1 | 0.04 | 1.90 | 1.88 | 0.22 |

*Except p24 data is only 3 lobes.

*These values represent standard deviations of corresponding rows in Table 7a.

We claim:

1. A method of determining characteristics of viral infection and pathology comprising:
   a. providing a culture of intact unstimulated human thymic lobules;
   b. incubating the culture under conditions suitable to maintain cell viability;
   c. exposing the lobules culture to a virus capable of infecting the lobules;
   d. observing the cells from the lobules for viral activity; and
   e. comparing the observations of step d with a hypothetical mechanism.

2. The method according to claim 1 wherein the thymic lobules are human fetal.

3. The method according to claim 1 wherein the thymic lobules are human neonate.

4. The method according to claim 1 wherein the thymic lobules are human adolescent or adult.

5. The method according to claim 1 wherein the lobules are contained in about 1 mm³ fragments containing 1–4 intact lobules.

6. The method according to claim 1 wherein the initial culturing step is for about 6–10 days.

7. The method according to claim 1 wherein the lobules are infected by incubation in a liquid containing the virus particles for a length of time suitable to allow infection.

8. The method according to claim 7 wherein the lobules are incubated in the liquid for approximately 2 hours.

9. The method according to claim 7 wherein the lobules are infected by dripping virus-containing liquid over the lobules.

10. The method according to claim 1 wherein the virus used for infection is selected from the group consisting of human cytomegalovirus, human immunodeficiency virus, herpes simplex virus, and rubella virus.

* * * * *

UNITED STATES PATENT AND TRADEMARK OFFICE

CERTIFICATE OF CORRECTION

PATENT NO. : 5,601,975

DATED : February 11, 1997

INVENTOR(S) : Mark L. Bonyhadi, Joseph M. McCune and Hideto Kaneshima

It is certified that error appears in the above-identified patent and that said Letters Patent is hereby corrected as shown below:

Column 12, line 15 the words "of control lobules culture" should be deleted.

Signed and Sealed this

Third Day of June, 1997

Attest:

BRUCE LEHMAN

*Attesting Officer*      *Commissioner of Patents and Trademarks*